US006495677B1

(12) United States Patent
Ramasamy et al.

(10) Patent No.: US 6,495,677 B1
(45) Date of Patent: *Dec. 17, 2002

(54) NUCLEOSIDE COMPOUNDS

(76) Inventors: Kanda S. Ramasamy, ICN Pharmaceuticals, Inc., 3300 Hyland Ave., Costa Mesa, CA (US) 92626; Guangyi Wang, ICN Pharmaceuticals, Inc., 3300 Hyland Ave., Costa Mesa, CA (US) 92626; Johnson Lau, ICN Pharmaceuticals, Inc., 3300 Hyland Ave., Costa Mesa, CA (US) 92626

( * ) Notice: Subject to any disclaimer, the term of this patent is extended or adjusted under 35 U.S.C. 154(b) by 111 days.

This patent is subject to a terminal disclaimer.

(21) Appl. No.: 09/594,410

(22) Filed: Jun. 16, 2000

Related U.S. Application Data

(60) Provisional application No. 60/182,676, filed on Feb. 15, 2000, and provisional application No. 60/189,672, filed on Mar. 15, 2000.

(51) Int. Cl.$^7$ ............... C07H 19/04; C07H 19/052; C07H 19/056
(52) U.S. Cl. ............... 536/28.6; 536/28.7; 536/28.8
(58) Field of Search ............... 536/28.6, 28.7, 536/28.8

(56) References Cited

U.S. PATENT DOCUMENTS

| 3,798,209 A | 3/1974 | Witkowski et al. | 536/28.7 |
| 3,984,396 A | 10/1976 | Witkowski et al. | 536/28.7 |
| 3,991,078 A | 11/1976 | Witkowski et al. | 536/28.7 |
| 4,093,624 A | 6/1978 | Revankar et al. | 536/28.7 |
| RE29,835 E | 11/1978 | Witkowski et al. | 536/28.7 |
| 6,130,326 A | 10/2000 | Ramasamy et al. | 536/28.7 |

FOREIGN PATENT DOCUMENTS

| JP | 64-26593 A | 1/1989 |

OTHER PUBLICATIONS

Srivastava et al. (I), "Synthesis and Antiviral Activity of Certain Thiazole C–nucleosides," *Journal of Medicinal Chemistry*, 20(2), 256–262 (Feb. 1977).

Srivastava et al. (II), "Synthesis and Antitumor Activity of 2–β–D–Ribofuranosylselenazole–4–carboxamide and Related Compounds," *Journal of Medicinal Chemistry*, 26(3), 445–448 (Mar. 1983).

Berry et al., "Synthesis and Biological Activity of the Novel Adenosine Analogs . . . ," *Nucleosides Nucleotides*, 13(1–3), 405–420 (1994); *Chemical Abstracts*, 121, Abstract No. 57865 (1994); only abstract supplied.

Sanghvi et al., "Growth Inhibition and Induction of Cellular Differentiation of Human Myeloid Leukemia Cells in Culture by Carbamoyl Congeners of Ribavirin," *Journal of Medicinal Chemistry*, 33(1), 336–344 (Jan., 1990); *Chemical Abstracts*, 112, Abstract No. 36356 (1990); only abstract supplied.

Ramasamy et al.(II), "Nucleoside Peptides. 8. Synthesis of Certain Peptide Derivatives of Ribavirin and Tiazofurin," *Nucleosides Nucleotides*, 6(5), 901–911 (1987); *Chemical Abstracts*, 109, Abstract No. 129625 (1988); only abstract supplied.

Hanna et al., "Synthesis of Certain 5'–Substituted Derivatives of Ribavirin and Tiazofurin," *Nucleosides Nucleotides*, 5(4), 343–362 (1986); *Chemical Abstracts*, 106, Abstract No. 214276 (1987); only abstract supplied.

*Primary Examiner*—James O. Wilson
*Assistant Examiner*—Lawrence E Crane
(74) *Attorney, Agent, or Firm*—Rutan & Tucker, LLP; Robert D. Fish

(57) ABSTRACT

Nucleosides, novel nucleoside analog compounds and their novel prodrug forms are disclosed. The novel compounds, prodrugs, or pharmaceutically acceptable esters or salts thereof may be used in pharmaceutical compositions, and such compositions may be used to treat an infection, an infestation, a neoplasm, or an autoimmune disease. The novel compounds may also be used to modulate aspects of the immune system, including modulation of Type 1 and Type 2 activity.

7 Claims, 2 Drawing Sheets

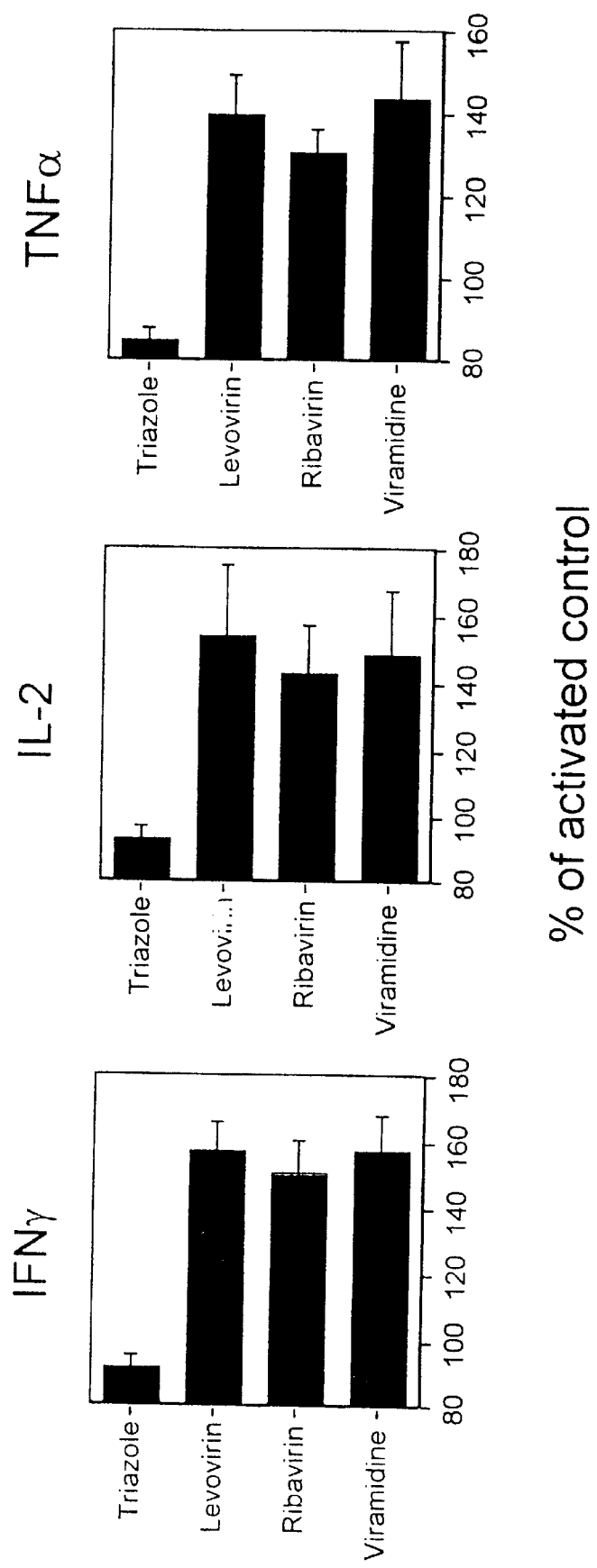
FIGURE 1 - The effect of viramidine, ribavirin and levovirin on Type 1 cytokine synthesis in SEB-activated human T cells

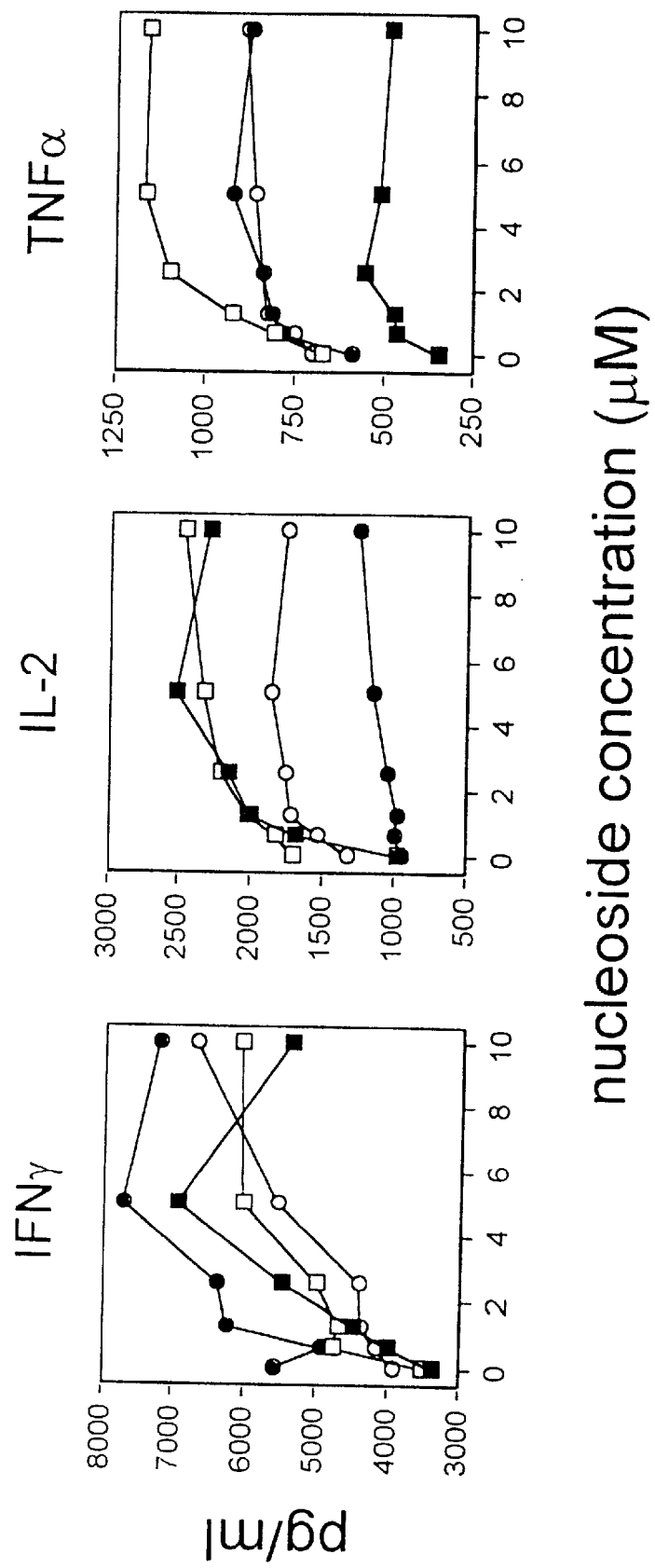
FIGURE 2 - The effect of 0.625 - 10μM viramidine on Type 1 cytokine synthesis in SEB-activated human T cells

NUCLEOSIDE COMPOUNDS

This application claims the benefit of U.S. provisional application Nos. 60/182,676 filed Feb. 15, 2000 and 60/189,672 filed Mar. 15, 2000, incorporated herein by reference in their entirety.

FIELD OF THE INVENTION

The present invention relates to the field of nucleoside compounds and nucleoside analog compounds.

BACKGROUND OF THE INVENTION

A nucleoside comprises two parts: a) a heterocyclic nitrogenous base portion, termed a purine or pyrimidine; and b) a sugar portion. Nucleoside analogs are compounds that are similar in structure and composition to nucleosides, but one or more of the substituents differ from naturally occurring nucleosides.

Ribavirin (1-β-D-ribofuranosyl-1,2,4-triazole-3-carboxamide) is a nucleoside analog that has demonstrated efficacy in treating viral diseases both as monotherapy (respiratory syncytial virus, Hall, C. B.; McBride, J. T.; Walsh, E. E.; Bell, D. M.; Gala, C. L.; Hildreth, S.; Ten Eyck, L. G.; W. J. Hall. Aerosolized ribavirin treatment of infants with respiratory syncytial viral infection. *N. Engl. J Med.* 1983, 308, 1443–1447), and in combination therapy with interferon-alpha (hepatitis C virus, Reichard, O.; Norkrans, G.; Fryden, A.; Braconier, J-H.; Sonnerborg, A.; Weiland, O. Randomized, double blind, placebo controlled trial of interferon alpha 2B with and without ribavirin for chronic hepatitis C. *Lancet* 1998, 351, 83–87). Recently reported studies indicate that the in vivo utility of ribavirin can result not only from direct inhibition of viral replication, but also from its ability to enhance T cell-mediated immunity (Hultgren, C.; Milich, D. R.; Weiland, O.; Sallberg, M. The antiviral compound ribavirin modulates the T helper Type1/Type2 subset balance in hepatitis B and C virus-specific immune responses. *J. Gen. Virol.* 1998, 79, 2381–2391; Ning, Q.; Brown, D.; Parodo, J.; Cattral, M.; Fung, L.; Gorczynski, R.; Cole, E., Fung, L.; Ding, J. W.; Liu, M. F.; Rotstein, O.; Phillips, M. J.; Levy, G. ribavirin inhibits viral-induced macrophage production of tumor necrosis factor, interleukin-1, procoagulant activity fg12 prothronibinase and preserves Th1 cytokine production but inhibits Th2 cytokine response. *J. Immunol.* 1998, 160, 3487–3493; Martin, M. J.; Navas, S.; Quiroga, J. A.; Pardo, M.; Carreno, V. Effects of the ribavirin-interferon alpha combination on cultured peripheral blood mononuclear cells from chronic hepatitis C patients. *Cytokine* 1998, 79, 2381–2391. This immunomodulatory effect of ribavirin is demonstrable in vitro by measuring the levels of Type 1 cytokines produced by activated T cells from both humans and mice (Tam, R. C.; Pai, B.; Bard, J.; Lim, C.; Averett, D. R.; Phan, U. T.; Milovanovic, T. ribavirin polarizes human T cell responses towards a Type 1 cytokine profile. *J. Hepatol.* 1999, 30, 376–382), and by other measures. The induction of a Type 1 cytokine bias by ribavirin is functionally significant in vivo in murine systems (Tam, R. C.; Lim, C.; Bard, J.; Pai, B. Contact hypersensitivity responses following ribavirin treatment in viva are influenced by Type 1 cytokine polarization, regulation of IL-10 expression and costimulatory signaling. *J. Immunol.* 1999, 163, 3709–3717).

Mammalian immune systems contain two major classes of lymphocytes: B lymphocytes (B cells), which originate in the bone marrow; and T lymphocytes (T cells) that originate in the thymus. B cells are largely responsible for humoral immunity (i.e., antibody production), while T cells are largely responsible for cell-mediated immunity.

T cells are generally considered to fall into two subclasses, helper T cells and cytotoxic T cells. Helper T cells activate other lymphocytes, including B cells and cytotoxic T cells, and macrophages, by releasing soluble protein mediators called cytokines that are involved in cell-mediated immunity. As used herein, lymphokines are a subset of cytokines.

Helper T cells are also generally considered to fall into two subclasses, Type 1 and Type 2. Type 1 cells produce interleukin 2 (IL-2), tumor necrosis factor (TNFα) and interferon gamma (IFNγ), and are responsible primarily for cell-mediated immunity such as delayed type hypersensitivity and antiviral immunity. In contrast, Type 2 cells produce interleukins, IL4, IL5, IL-6, IL-9, IL-10 and IL-13, and are primarily involved in assisting humoral immune responses such as those seen in response to allergens, e.g. IgE and IgG4 antibody isotype switching (Mosmann, 1989, *Annu Rev Immunol.* 7:145–173).

As used herein, the terms Type 1 and Type 2 "responses" are meant to include the entire range of effects resulting from induction of Type 1 and Type 2 lymphocytes, respectively. Among other things, such responses include variation in production of the corresponding cytokines through transcription, translation, secretion, and possibly other mechanisms, increased proliferation of the corresponding lymphocytes, and other effects associated with increased production of cytokines, including motility effects.

Previous applications (e.g., 09/291903, now U.S. Pat. No. 6,130,326) which is incorporated herein by reference, relates to aspects of our recent discoveries involving the effect of various nucleosides (which are defined herein to include derivatives and analogs of native nucleosides) on selectively modulating lymphocyte responses relative to each other. Among other things, we have shown that either of Type 1 and Type 2 responses can be selectively suppressed while the other is either induced or left relatively unaffected, and either of Type 1 or Type 2 responses can be selectively induced while the other is either suppressed or left relatively unaffected. We have also discovered the surprising fact that some nucleosides effective in selectively modulating Type 1 and Type 2 responses relative to one another tend to have a bimodal effect. Among other things, some nucleosides that tend to generally suppress or induce both Type 1 and Type 2 activity at a relatively higher dose tend to selectively modulate Type 1 and Type 2 relative to each other at relatively lower doses.

Viramidine (1-β-D-ribofuranosyl-1,2,4-triazole-3-carboxamidine hydrochloride) has been shown active in ten different viruses that are comparable to ribavirin. (J. T. Witkowski, R. K. Robins, G. P. Khare, R. W. Sidwell, *J. Med. Chem.*, 16, 935–937, 1973; R. W. Sidwell, J. H. Huffman, D. L. Barnard, D. Y. Pifat, *Antiviral Research*, 10, 193–208, 1988; B. Gabrielsen, M. J. Phelan, L. Barthel-Rosa, C. See, J. W. Huggins, D. F. Kefauver, T. P. Monath, M. A. Ussery, G.

N. Chmurny, E. M. Schubert, K. Upadhya, C. Kwong, D. A. Carter, J. A. Secrist III, J. J. Kirsi, W. M. Shannon, R. W. Sidwell, G. D. Kini, R. K. Robins, *J. Med. Chem.*, 35, 3231–3238, 1992). In addition, Viramidine™, like ribavirin, is an inhibitor of IMP dehydrogenase (R. C. Willis, R. K. Robins, J. E. Seegmiller, *Molecular Pharmacology*, 18, 287–295, 1980). Furthermore, preliminary toxicology studies suggest that Viramidine™ is less toxic than ribavirin (D.

Y. Pifat, R. W. Sidwell, P. G. Canonico, *Antiviral Research*, 9, 136, 1988). Also, recent studies at our lab (R. Tam, K. Ramasaniy, ICN Pharmaceuticals, Inc., unpublished results, 1999) revealed that Viramidine™ and ribavirin exhibited similar immunomodulatory properties. These results coupled with low bioavailability and the toxicity associated with ribavirin prompt us not only to develop Viramidine™ for other viral diseases but also to prepare other derivatives of viramidine, including the synthesis of prodrugs of viramidine, and screen them as potential antiviral agents.

Ribavirin and Levovirin™ are similar with respect to structure, except that Levovirin™ is the L-configuration of the compound and has a substantially reduced toxicity. For example, while oral administration of ribavirin in rats at 180 mg/kg over four weeks produced significant hemolytic anemia and leukopenia, Levovirin™ did not produce any observable clinical pathology. Furthermore, it is contemplated that treatment of a viral disease with Levovirin™ is predominantly based on the modulation of the Th1/Th2 balance towards a Th1 dominated response, and not predominantly based an a direct antiviral effect. The term "direct antiviral" effect or activity as used herein refers to an immediate effect or activity of a drug on viral assembly or replication. In contrast, a reduction of viral activity or replication that is at least in part mediated by one or more components of the immune system is not considered a "direct antiviral" effect or activity. Likewise, it should be appreciated that a relative reduction of the Th2 response during a treatment may be especially advantageous in diseases that are correlated with an increased Th2 response (e.g., HCV infection).

The effect of other nucleoside analog compounds on selectively modulating lymphocyte responses relative to each other has not been previously studied or documented. We have discovered that the bimodal effect, or selective modulation of Type 1 and Type 2 responses relative to one another, also occurs after administration of other nucleoside analog compounds, such as pro-drug forms of the compounds.

There are many barriers to overcome in developing biologically active compounds into clinically useful agents. Many potent biologically active compounds never become clinically useful agents because of their undesirable biopharmaceutical properties which include low bioavailability due to low permeability through biological barriers, such as the blood brain barrier (BBB) and the intestinal barrier. Although many factors affect the bioavailability of a drug, the undesirable physicochemical properties (e.g., charge, lipophilicity, hydrogen bonding potential, size) of many drugs is probably one of the most commonly encountered factors that hinder the permeation of drugs through biological barriers. Therefore, optimization of the physicochemical characteristics (charge, lipophilicity, hydrogen bonding potential, size) of a drug is probably the most likely general strategy to facilitate the transport of drugs through such membrane barriers.

To optimize the physicochemical properties of drugs, one possible strategy is that of prodrugs. (H. Bundgaard, *Design of Prodrugs*, Elsevier, Amsterdam, 1985; N. Bodor, L. Prokai, W. M. Wu, H. Farag, S. Jonalagadda, M. Kawamura, J. Simpkins, *Science*, 257, 1698–1700, 1992; H. E. Taylor, K. B. Sloan, *J. Pharm. Sci*, 87, 5–20, 1998). The term prodrug is used to describe an agent, which must undergo chemical or enzymatic transformation to the active or parent drug after administration, so that the metabolic product or parent drug can subsequently exhibit the desired pharmacological response. By derivatizing certain polar functional groups in small organic molecules transiently and bioreversibly, the undesirable physicochemical characteristics (e.g., charge, hydrogen bonding potential) of these groups have been "masked" without permanently altering the pharmacological properties of the molecules. This strategy has been very successfully used in cases where the prodrug derivatization involves converting a carboxyl or a hydroxyl functional group into an ester, which can be readily hydrolyzed in vivo either chemically, or enzymatically. The promising prodrug concept, we anticipate that the introduction of other moieties in the parent drug would increase the bioavailability, adsorption, and antiviral effects.

Despite the existence of as-yet undefined mechanisms, we have discovered that enormous potential benefits can be derived from selective modulation of Type 1 and Type 2 responses relative to each other. We have concluded, for example, that specific modulation of Type 1 relative to Type 2 can be useful in treating a wide variety of conditions and diseases, ranging from infections, infestations, tumors and hypersensitivities to autoimmune diseases.

These discoveries are especially significant because modem treatment strategies for many of the above-listed diseases have limited effectiveness, significant side effects, or both. Treatment of autoimmune disease, for example, is frequently limited to palliative measures, removal of toxic antibodies (as in myasthenia gravis), and administration of hazardous drugs including corticosteroids, chloroquine derivatives, and antimetabolic or antitumor drugs, and drugs such as cyclosporines that target immune system cells.

SUMMARY

The present invention is directed to novel nucleoside analog compounds and related compounds, such as prodrugs, their therapeutic uses and synthesis.

In one aspect of the invention, there are provided nucleosides, nucleoside analog compounds and nucleoside prodrugs of the generalized Formula 1, in which the sugar is either in the L-or D-conformation:

R—Nu where Nu is a nucleoside or nucleoside analog compound; and R, which may or may not be present, comprises a ligand, otherwise termed a substituent, that is designed to modify the nucleoside through modification of the sugar, the base, or in some cases both the sugar and the base.

In one aspect of the invention, there are provided nucleoside analog compounds and prodrugs of Formula 1, in which the sugar is either in the L- or D-conformation:

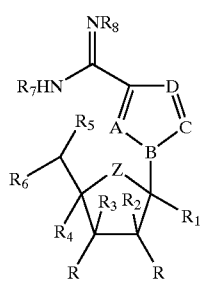

Formula 1 wherein: A, C and D are independently selected from N or C—$R_9$; $R_9$ is independently H, halogens, lower alkyl, alkenyl, alkynyl, amino, CN, SH, CHO, COOH, $CH_2OH$, vinyl halide or hydroxyl; Z is independently selected from O, $CH_2$ or S; R is independently selected from H, hydroxyl, protected hydroxyl or halogens; $R_1$, $R_2$, $R_3$, $R_4$, $R_5$, are independently selected from H, halogens, CN, $CH_2OH$, lower alkyl, vinyl or acetylene; when $R_2$ is hydroxyl, then, R that is attached to the same carbon as that of $R_2$ is not halogen; when $R_3$ is hydroxyl, then, R that is attached to the same carbon as that of $R_3$ is not halogen; $R_6$ is independently selected from H, hydroxyl, protected hydroxyl, —$CH_2OH$, —$CH_2PO(OH)_2$—, O-amino acids, O-retinoic acid, O-cholesteral, O-cholic acid, O-coumarinic acid, O-salicylic acid, O-succinic acid, O-bile acid, O-lipids, O—P(O)—(O—$CH_2$—$CH_2$—S—CO—$CH_3$)$_2$; O-steroids; O-monophosphate derivatives, O-diphosphate derivatives or O-triphosphate derivatives; $R_7$ is independently selected from H, alkyl, $CH_3COO$—, $CH_3COO$-Phenyl-$CH_2$—O—CO—, phenyl, —$(CH_2)n$—COOH, coumarinic acid, salicylic acid, dithiosuccinoyl derivatives, reductase mediated cleavable groups, phosphonoformic acid or phosphoramidates groups; $R_8$ is independently selected from H, HHCl, HHBr, lower alkyl, phenyl, $CH_3COO$—, $CH_3COO$-Phenyl-$CH_2$—O—CO—, phenyl, or —$(CH_2)n$—COOH; $R_7$ and $R_8$ combined are selected from cyclic structure or amino acids.

In another aspect of the invention, there are provided nucleoside analog compounds and prodrugs of Formula 3, in which the sugar is either in the L- or D-conformation:

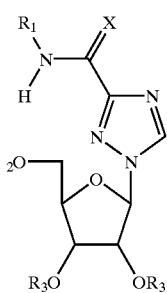

Formula 3 wherein X is O or NH; $R_1$ is a masking group of the amino group; $R_2$ is selected from H, HCO—, R—C(O)—, and $(R'O)_2P(O)$—O—, where R is C1–C17 alkyl alkenyl, or alkynyl group and R' is a masking group of the phosphate; $R_3$ is independently H or C1–C18 acyl; $R_1$ and $R_2$ are not hydrogen at the same time.

In another aspect of the invention, there are provided nucleoside analog Compounds and prodrugs of Formula 4, in which the sugar is either in the L- or D-conformation:

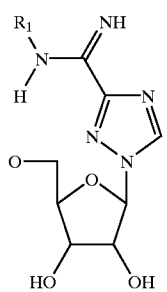

Formula 4 where R is a masking group having any of the following structures:

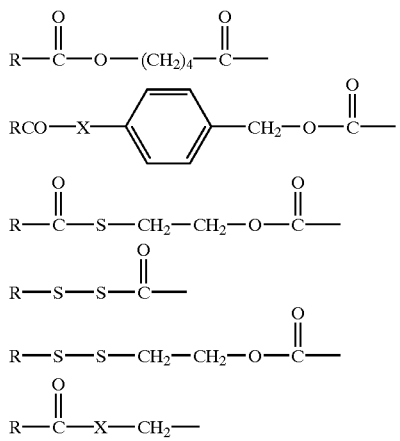

where X is O or S; R is C1–C18 alkyl, alkenyl, alkynyl, aryl, and aralkyl, straight or branched.

In another aspect of the invention, there are provided nucleoside analog compounds and prodrugs of Formula 5, in which the sugar is either in the L- or D-conformation:

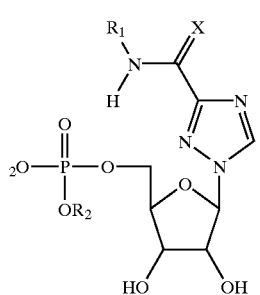

Formula 5 where R1 is H or a masking group as designated in claim 2; R2 is a masking group of the phosphate having any of the following structures:

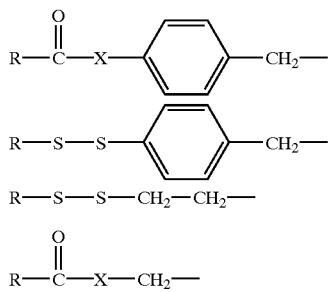

where X is O, or S; Ris C1–C18 alkyl, alkenyl, alkynyl, aryl, aralkyl straight or branched; R', R" are selected from H, alkyl, aryl but R' and R" are not hydrogen at the same time.

In another aspect of the invention, there are provided nucleoside analog compounds and prodrugs of Formula 6, in which the sugar is either in the L- or D-conformation:

Formula 6

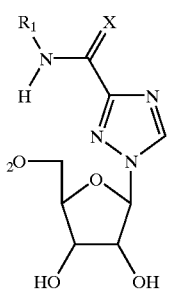

Formula 7

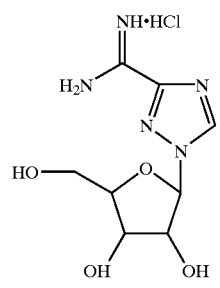

Viramidine-ICN 3142 where $R_1$ is H or a masking group as designated in claim 2; $R_2$ is a masking group of the phosphate having any of the following structures:

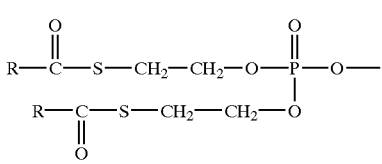

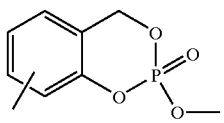

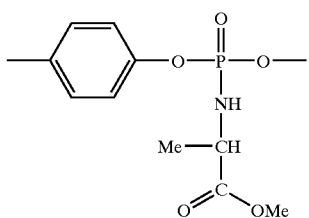

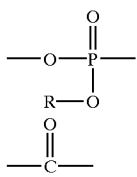

where R is C1–C18 alkyl, alkenyl, alkynyl, aryl, and aralkyl, straight or branched;

M is selected from alkyl, alkenyl, alkynyl, aralkyl, aryl, and a group of hydrophobic compounds such as cholesterol, vitamin D derivative, and cholic acid derivatives bearing a linker which can be covalently attached to the carbonyl group.

In yet another aspect of the invention, there are provided nucleoside analog compounds and prodrugs of Formula 7:

In another aspect of the invention, there are provided nucleoside analog compounds and prodrugs of Formula 8:

Formula 8

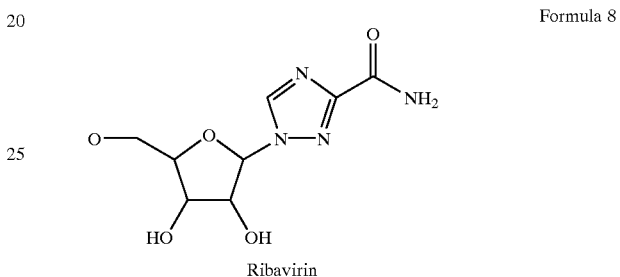

Ribavirin

In yet another aspect of the invention, there are provided nucleoside analog compounds and prodrugs of Formula 9:

Formula 9

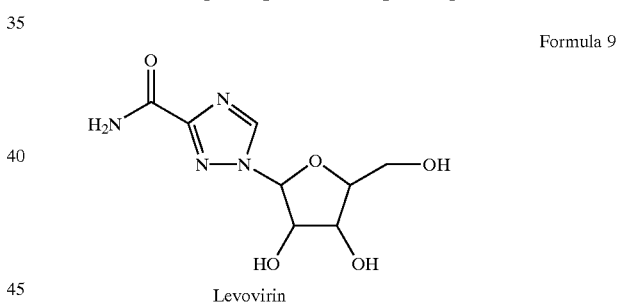

Levovirin

In another aspect of the invention, there are provided nucleoside analog compounds and prodrugs of Formula 10:

Formula 5

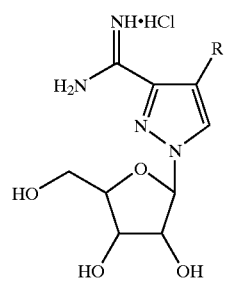

wherein: R is independently selected from hydrogen, halogens, amide, amidines, alkyl, phenyls, vinyl, or acetylene;

In another aspect of the invention, there are provided nucleoside analog compounds and prodrugs of Formula 11:

Formula 6

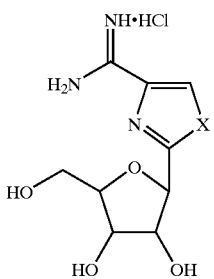

wherein: X is independently selected from oxygen, sulphur, Se or NR; R is independently selected from hydrogen, acetyl or alkyl; In another aspect of the invention, there are provided nucleoside analog compounds and prodrugs of Formula 12:

Formula 7

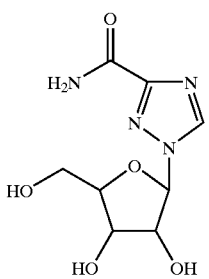

In yet another aspect of the invention, a pharmaceutical composition comprises a therapeutically effective amount of any one or a combination of Formulas 1–12, or a pharmaceutically acceptable ester or salt thereof admixed with at least one pharmaceutically acceptable carrier.

In yet another aspect of the invention, a pharmaceutical composition comprises a pro-drug form of any one or a combination of Formulas 1–12, or a pharmaceutically acceptable ester or salt thereof admixed with at least one pharmaceutically acceptable carrier.

In a further aspect of the invention, a compound according to any one of Formulas 1–12 are used in the treatment of any condition which responds positively to administration of the compound, and according to any formulation and protocol which achieves the positive response. Among other things, it is contemplated that compounds of Formulas 1–12 may be used to treat an infection, an infestation, a cancer, tumor or other neoplasm, giant cell arteritis, or an autoimmune disease.

BRIEF DESCRIPTION OF THE FIGURES

FIG. 1 is a graphical depiction of Viramidine™ (1.39 µg/ml), ribavirin (1.22 µg/ml), and Levovirin™ 1.22 µg/ml) on Type 1 cytokine synthesis in Staphylococcal Enterotoxin B-activated human T-cells. The data are mean and SEM for 7 donors.

FIG. 2 is a graphical depiction of the effect of 0.625–10 µM Viramidine™ on Type 1 cytokine synthesis in Staphylococcal Enterotoxin B-activated human T cells. The data represent 4 individual donors.

DETAILED DESCRIPTION

Where the following terms are used in this specification, they are used as defined below.

The terms "nucleoside" and "nucleoside analog compound" are interchangeable and refer to a compound composed of any pentose or modified pentose moiety attached to a specific position of a heterocycle, aromatic heterocycle or to the natural position of a purine (9-position) or pyrimidine (1-position) or to the equivalent position in an analog.

The term "nucleotide" refers to a phosphate ester substituted on the 5'-position of a nucleoside.

The term "heterocycle" refers to a monovalent saturated or unsaturated carbocyclic radical having at least one hetero atom, such as N, O or S, within the ring each available position of which can be optionally substituted, independently, with, e.g., hydroxy, oxo, amino, imino, lower alkyl, bromo, chloro and/or cyano. Included within this class of substituents are purines, pyrimidines.

The term "purine" refers to nitrogenous bicyclic heterocycles.

The term "pyrimidine" refers to nitrogenous monocyclic heterocycles.

The term "D-nucleosides" refers to the nucleoside compounds that have a D-ribose sugar moiety (e.g., Adenosine).

The term "L-nucleosides" refers to the nucleoside compounds that have an L-ribose sugar moiety.

The terms "L-configuration" and "D-configuration" are used throughout the present invention to describe the chemical configuration of the ribofuranosyl moiety of the compounds that is linked to the pyrrolo-pyrimidone portion of the molecule.

The term "C-nucleosides" is used throughout the specification to describe the linkage type that formed between the ribose sugar moiety and the heterocyclic base. In C-nucleosides, the linkage originates from the C-1 position of the ribose sugar moiety and joins the carbon of the heterocyclic base. The linkage that forms in C-nucleosides is carbon-to-carbon type.

The term "N-nucleosides" is used throughout the specification to describe the linkage type that formed between the ribose sugar moiety and the heterocyclic base. In N-nucleosides, the linkage originates from the C-1 position of the ribose sugar moiety and joins the nitrogen of the heterocyclic base. The linkage that forms in N-nucleosides is carbon to nitrogen type.

The term "protecting group" refers to a chemical group that is added to, oxygen or nitrogen atom to prevent its further reaction during the course of derivatization of other moieties in the molecule in which the oxygen or nitrogen is located. A wide variety of oxygen and nitrogen protecting groups are known to those skilled in the art of organic synthesis.

The term "lower alkyl" refers to methyl, ethyl, n-propyl, isopropyl, n-butyl, t-butyl, i-butyl, or n-hexyl. This term is further exemplified to a cyclic, branched or straight chain from one to six carbon atoms.

The term "aryl" refers to a monovalent unsaturated aromatic carbocyclic radical having a single ring (e.g., phenyl) or two condensed rings (e.g., naphthyl), which can optionally be substituted with hydroxyl, lower alky, chloro, and/or cyano.

The term "heterocycle" refers to a monovalent saturated or unsaturated carbocyclic radical having at least one hetero atom, such as N, O, S, Se or P, within the ring, each available position of which can be optionally substituted or unsubstituted, independently, with hydroxy, oxo, amino, imino, lower alkyl, bromo, chloro, and/or cyano.

The term "monocyclic" refers to a monovalent saturated carbocyclic radical having at least one hetero atom, such as O, N, S, Se or P, within the ring, each available position of which can be optionally substituted, independently, with a sugar moiety or any other groups like bromo, chloro and/or cyano, so that the monocyclic ring system eventually aromatized [e.g., Thymidine].

The terms "immunomodulator" and "modulator" are herein used interchangeably and refers to natural or synthetic products capable of modifying the normal or aberrant immune system through stimulation or suppression.

The term "effective amount" refers to the amount of a compound of formula (I) that will restore immune function to normal levels, or increase immune function above normal levels in order to eliminate infection.

The compounds of Formulas 1–12 may have multiple asymmetric centers. Accordingly, they may be prepared in either optically active form or as a racemic mixture. The scope of the invention as described and claimed encompasses the individual optical isomers and non-racemic mixtures thereof as well as the racemic forms of the compounds of Formulas 1–12.

The term "α" and "β" indicate the specific stereochemical configuration of a substituent at an asymmetric carbon atom in a chemical structure as drawn.

The term "enantiomers" refers to a pair of stereoisomers that are non-superimposable mirror images of each other. A mixture of a pair of enantiomers, in a 1:1 ratio, is a "racemic" mixture.

The term "isomers" refers to different compounds that have the same formula. "Stereoisomers" are isomers that differ only in the way the atoms are arranged in space.

"Pharmaceutically acceptable salts" may be any salts derived from inorganic and organic acids or bases.

Compounds

The present invention is directed to novel nucleoside analog compounds and related compounds, such as prodrugs, their therapeutic uses and synthesis.

In one aspect of the invention, there are provided nucleosides, nucleoside analog compounds and nucleoside prodrugs of the generalized Formula 1, in which the sugar is either in the L- or D-conformation:

R—Nu where Nu is a nucleoside or nucleoside analog compound; and R, which may or may not be present, comprises a ligand, otherwise termed a substituent, that is designed to modify the nucleoside through modification of the sugar, the base, or in some cases both the sugar and the base.

In one aspect of the invention, there are provided nucleoside analog compounds and prodrugs of Formula 1, in which the sugar is either in the L- or D-conformation:

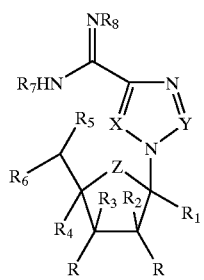

Formula I wherein: X and Y are independently selected from N or C—Rg; $R_9$ is independently H, halogens, lower alkyl or hydroxyl; Z is independently selected from O or S; R is independently selected from H, hydroxyl, or protected hydroxyl; $R_1$, $R_2$, $R_3$, $R_4$, $R_5$, are independently selected from H, halogens, CN, lower alkyl, vinyl or acetylene; when $R_2$ is hydroxyl, then, R that is attached to the same carbon as that of $R_2$ is not halogen; when $R_3$ is hydroxyl, then, R that is attached to the same carbon as that of $R_3$ is not halogen; $R_6$ is independently selected from H, hydroxyl, protected hydroxyl, —$CH_2OH$, —$CH_2PO(OH)_2$—, O-amino acids, O-retinoic acid, O-cholesterol, O-lipids, O—P(O)—(O—$CH_2$—$CH_2$—S—CO—$CH_3$)$_2$; O-steroids; O-monophosphate, O-diphosphate or O-triphosphate; $R_7$ is independently selected from H, alkyl, $CH_3COO$—, $CH_3COO$-Phenyl-$CH_2$—OCO—, phenyl, or —(CH$_2$)n—COOH; $R_8$ is independently selected from H, HHCl, HHBr, lower alkyl, phenyl, $CH_3COO$—, $CH_3COO$-Phenyl-$CH_2$—O—CO—, phenyl, or —(CH$_2$)n—COOH; $R_7$ and $R_8$ combined are selected from cyclic structure or amino acid.

In another aspect of the invention, there are provided nucleoside analog compounds and prodrugs of Formula 3, in which the sugar is either in the L- or D-conformation:

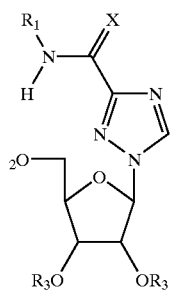

Formula 3 wherein X is O or NH; $R_1$ is a masking group of the amino group; $R_2$ is selected from H, HCO—, R—C(O)—, and (R'O)$_2$P(O)—O—, where R is C1–C17 alkyl alkenyl, or alkynyl group and R' is a masking group of the phosphate; $R_3$ is independently H or C1–C18 acyl; and $R_1$ and $R_2$ are not hydrogen at the same time.

In another aspect of the invention, there are provided nucleoside analog compounds and prodrugs of Formula 4, in which the sugar is either in the L- or D-conformation:

Formula 4

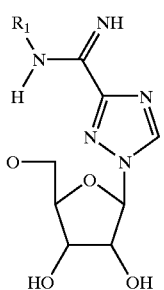

where R is a masking group having any of the following structures:

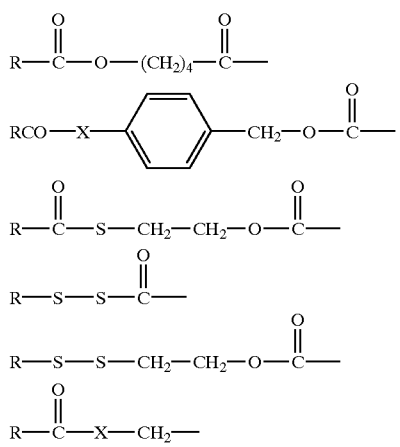

where X is O or S; R is C1–C18 alkyl, alkenyl, alkynyl, aryl, and aralkyl, straight or branched.

In another aspect of the invention, there are provided nucleoside analog compounds and prodrugs of Formula 5, in which the sugar is either in the L- or D-conformation:

Formula 5

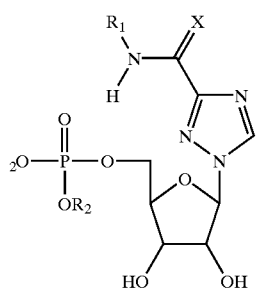

where $R_1$ is H or a masking group as designated in claim 2; $R_2$ is a masking group of the phosphate having any of the following structures:

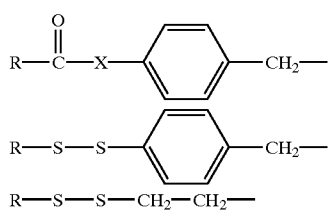

-continued

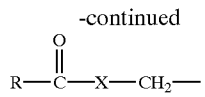

where X is O, or S; R is C1–C18 alkyl, alkenyl, alkynyl, aryl, aralkyl straight or branched; R', R" are selected from H, alkyl, aryl but R' and R" are not hydrogen at the same time.

In another aspect of the invention, there are provided nucleoside analog compounds and prodrugs of Formula 6, in which the sugar is either in the L- or D-conformation:

Formula 6

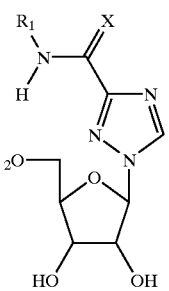

where $R_1$ is H or a masking group as designated in claim 2; $R_2$ is a masking group of the phosphate having any of the following structures:

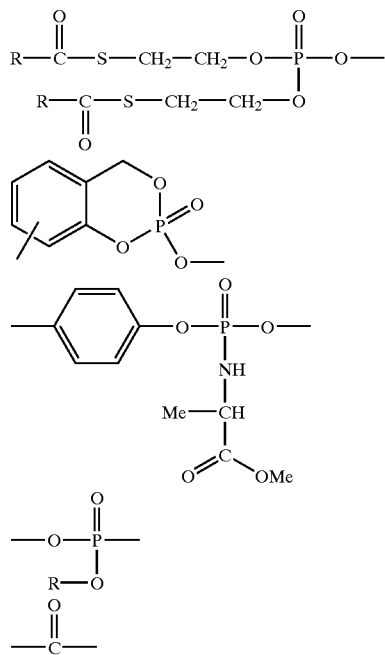

where R is C1–C18 alkyl, alkenyl, alkynyl, aryl, aralkyl straight or branched; M is selected from alkyl, alkenyl, alkynyl, aralkyl, aryl, and a group of hydrophobic compounds such as cholesterol, vitamin D derivative, cholic acid derivatives bearing a linker which can be covalently attached to the carbonyl group.

In yet another aspect of the invention, there are provided nucleoside analog compounds and prodrugs of Formula 7:

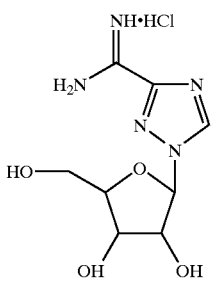

Viramidine – ICN 3142

In another aspect of the invention, there are provided nucleoside analog compounds and prodrugs of Formula 8:

Formula 8

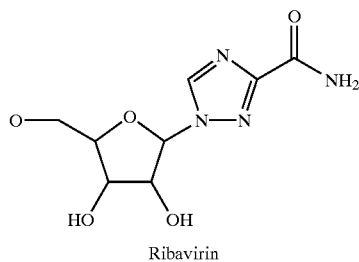

Ribavirin

In yet another aspect of the invention, there are provided nucleoside analog compounds and prodrugs of Formula 9:

Formula 9

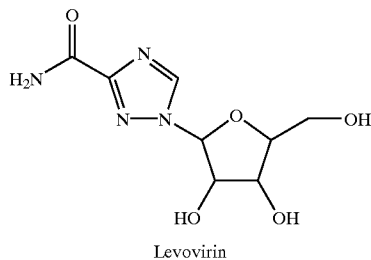

Levovirin

In another aspect of the invention, there are provided nucleoside analog compounds and prodrugs of Formula 10:

Formula 10

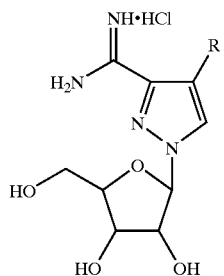

wherein: R is independently selected from hydrogen, halogens, amide, amidines, alkyl, phenyls, vinyl, or acetylene.

In another aspect of the invention, there are provided nucleoside analog compounds and prodrugs of Formula 11:

Formula 11

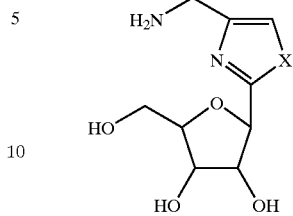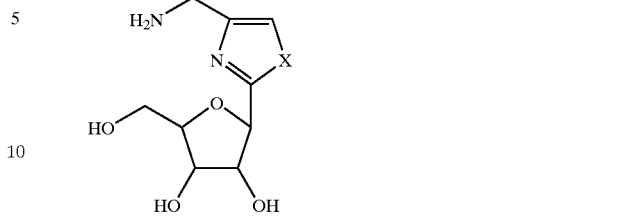

wherein: X is independently selected from oxygen, sulphur, Se or NR; R is independently selected from hydrogen, acetyl, or alkyl.

In another aspect of the invention, there are provided nucleoside analog compounds and prodrugs of Formula 12:

Formula 12

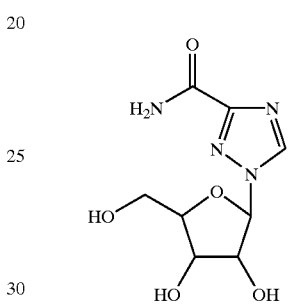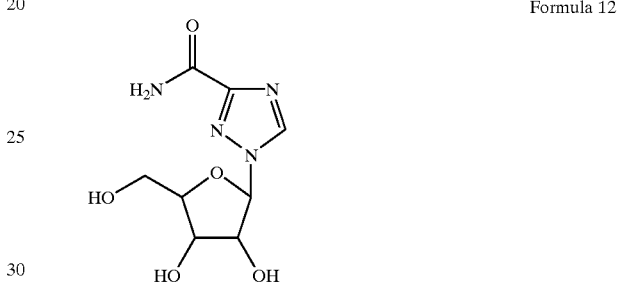

Uses

It is contemplated that compounds according to Formulas 1–9, the compounds of the present invention, will be used to treat a wide variety of conditions, and in fact any condition which responds positively to administration of one or more of the compounds. Among other things it is specifically contemplated that compounds of the invention may be used to treat an infection, an infestation, a cancer or tumor or an autoimmune disease. It is further contemplated that the compounds of the invention may be used to target conditions or diseases in specific organs of a patient, such as the liver or heart.

Infections contemplated to be treated with the compounds of the present invention include respiratory syncytial virus (RSV), hepatitis B virus (HBV), hepatitis C virus (HCV), herpes simplex type 1 and 2, herpes genitalis, herpes keratitis, herpes encephalitis, herpes zoster, human immunodeficiency virus (HIV), influenza A virus, hantann virus (hemorrhagic fever), human papilloma virus (HPV), measles, and fungus.

Infestations contemplated to be treated with the compounds of the present invention include protozoan infestations, as well as helminth and other parasitic infestations.

Cancers or tumors contemplated to be treated include those caused by a virus, and the effect may involve inhibiting the transformation of virus-infected cells to a neoplastic state, inhibiting the spread of viruses from transformed cells to other normal cells and/or arresting the growth of virus-transformed cells.

Autoimmune and other diseases contemplated to be treated include arthritis, psoriasis, bowel disease, juvenile diabetes, lupus, multiple sclerosis, gout and gouty arthritis, rheumatoid arthritis, rejection of transplantation, giant cell arteritis, allergy and asthma.

Still other contemplated uses of the compounds according to the present invention include use as intermediates in the chemical synthesis of other nucleoside or nucleotide analogs that are, in turn, useful as therapeutic agents or for other purposes.

In yet another aspect, a method of treating a mammal comprises administering a therapeutically and/or prophylactically effective amount of a pharmaceutical containing a compound of the present invention. In this aspect the effect may relate to modulation of some portion of the mammal's immune system, especially modulation of lymphokines profiles of Type 1 and Type 2 with respect to one another. Where modulation of Type 1 and Type 2 lymphokines occurs, it is contemplated that the modulation may include suppression of both Type 1 and Type 2, or suppression of Type 1 and stimulation of Type 2.

In general, the most preferred uses according to the present invention are those in which the active compounds are relatively less cytotoxic to the non-target host cells and relatively more active against the target. In this respect, it may also be advantageous that L-nucleosides may have increased stability over D-nucleosides, which could lead to better phannacokinetics. This result may attain because L-nucleosides may not be recognized by enzymes, and therefore may have longer half-lives.

It is contemplated that compounds according to the present invention will be administered in any appropriate pharmaceutical formulation, and under any appropriate protocol. Thus, administration may take place orally, parenterally (including subcutaneous injections, intravenous, intramuscularly, by intrastemal injection or infusion techniques), by inhalation spray, or rectally, topically and so forth, and in dosage unit formulations containing conventional non-toxic pharmaceutically acceptable carriers, adjuvants, and vehicles.

By way of example, it is contemplated that compounds according to the present invention can be formulated in admixture with a pharmaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in patients.

In certain pharmaceutical dosage forms, the pro-drug form of the compounds, especially including phosphonated prodrug forms, acylated (acetylated or other) derivatives, esters and pyridine esters and various salt forms of the present compounds are preferred and can be administered in a method of treatment of a condition of a patient. One of ordinary skill in the art will recognize how to readily modify the present compounds to pro-drug forms to facilitate delivery of active compounds to a target site within the host organism or patient. One of ordinary skill in the art will also take advantage of favorable pharmacokinetic parameters of the pro-drug forms, where applicable, in delivering the present compounds to a targeted site within the host organism or patient to maximize the intended effect of the compound.

The formation of desirable prodrug compounds takes place through the modification of either the sugar portion or the base portion of the nucleoside. The sugar and/or the base portions can be modified by 1) placing substituents at different positions on the sugar or base of the compound; 2) placing different chemical substituents, or ligands, at a particular position on the sugar or base of the compound; and/or 3) designing the substituent placement and makeup around the target desired, such as the liver, brain or stomach, thus creating a "target-specific" compound.

Substituents, or ligands, can be placed at different positions on the sugar or base of the compound. In preferred embodiments, the substituents or ligands can be placed on the 3, 4, 5, or 5' position of the sugar portion of the nucleoside. In other preferred embodiments, the substituents or ligands can be placed on the base portion of the nucleoside to modify the base portion of the nucleoside without disrupting the aromaticity or conjugation within the purine or pyrimidine base rings.

Different chemical substituents, or ligands, can be covalently linked to a particular position on the sugar and/or base of the compound. The ligands or substituents can comprise components that are designed to be drugs or components that are designed to be non-drugs. The ligands or substituents can also comprise components that are designed to be active components or inert components. The ligands or substituents can also be designed to comprise a certain size or length, or even to reflect a specific polarity. Contemplated ligands include alkyl, alkylene, alcohols, amines, amides, sulfones, sulfides, esters, ketones, carboxylic acids, metal ions, transition metal ions, aromatic compounds, heterocyclic aromatic compounds, cyclic compounds, heterocyclic compounds, and heteroacyclic compounds.

The prodrug form of the nucleoside can also be designed to be "target-specific", meaning that the entire composition of the molecule, including additional substituents or ligands, has been designed to target a particular part of a patient, such as the liver, brain, or stomach. The prodrug form of the nucleoside can also be modified or designed to become reactive or react intracellularly or extracellularly.

A contemplated example of the formation of a pro-drug form of the compounds disclosed herein is as follows. One of the simplest prodrug forms of Viramidine™ is the tri-O-acetyl derivative of viramidine. Viramidine may be replaced in the following example with ribavirin, Levovirin™, or any of the other contemplated nucleosides of the present inventive subject matter.

Scheme 1

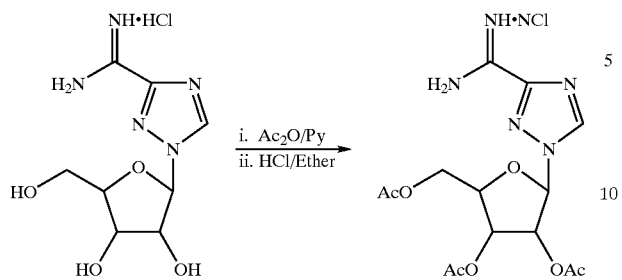

5'-Retinoyl derivative of Viramidine™ is another simple prodrug and been prepared as follows:

Scheme 2

Retinoic  i. (COCl)$_2$
         ii. Viramidine/DMAP
         iii. HCl/Ether

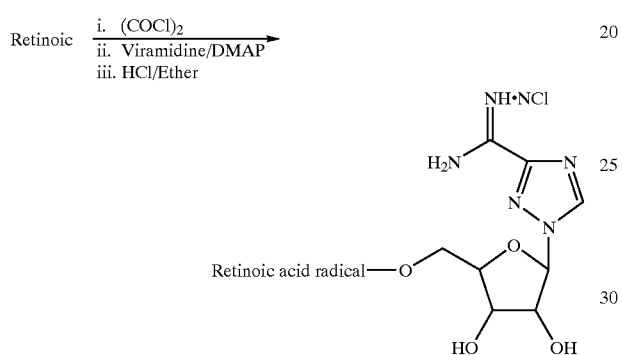

Other 5'-derivatives of Viramidine™ includes the following. Most of these compounds may be obtained as described (C. Sergheraert, C. Pierlot, A. Tartar, Y. Henin, M. Lemaitre, *J. Med. Chem.*, 36, 826–830, 1993).

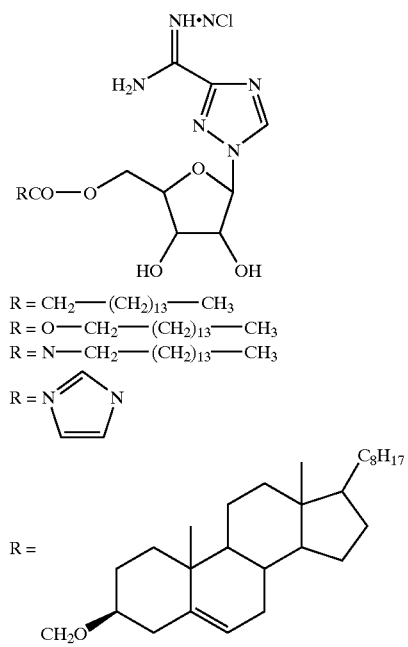

R = CH$_2$—(CH$_2$)$_{13}$—CH$_3$
R = O—CH$_2$—(CH$_2$)$_{13}$—CH$_3$
R = N—CH$_2$—(CH$_2$)$_{13}$—CH$_3$

Other groups for R include bile acids, lipids, cholic acid, cholesterol derivatives, and vitamins. Synthesis of salicylic-based prodrug of Viramidine™ may be obtained as follows:

Scheme 4

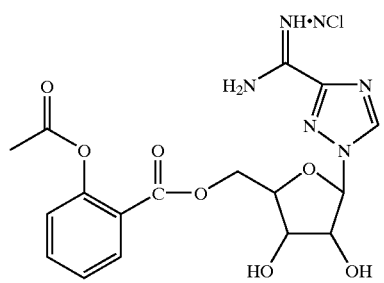

Amino acid esters are considered yet another class of prodrugs can be synthesized as shown below:

Scheme 5

Z-Amino Acid  i. EDC/DMAP/Viramidine
              ii. Pd/C/HCl/Dioxane

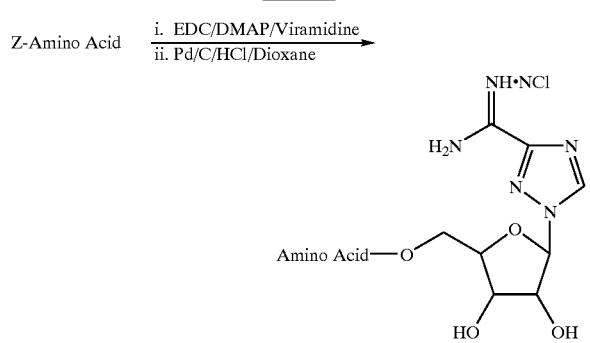

For specific delivery of drugs to the liver and the biliary system the endogenous bile acid transport system is an attractive candidate. Synthesis of bile acid conjugates of Viramidine™ could be accomplished as represented below:

Scheme 6

Cholic Acid  i. EDC/DMAP/Viramidine
             ii. HCl/Dioxane

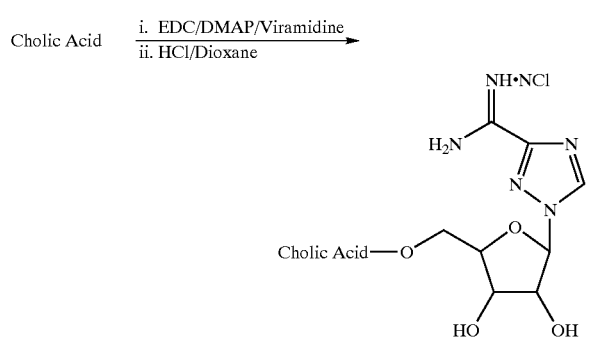

Nucleotide derivatives are another class of prodrugs. Preparation of protected 5'-monophosphate derivatives are shown in Scheme 7. Protecting the negative charges of phosphates with neutral substituents would form more lipophilic derivatives, which is expected to revert back to the corresponding monophosphates once inside a living cell.

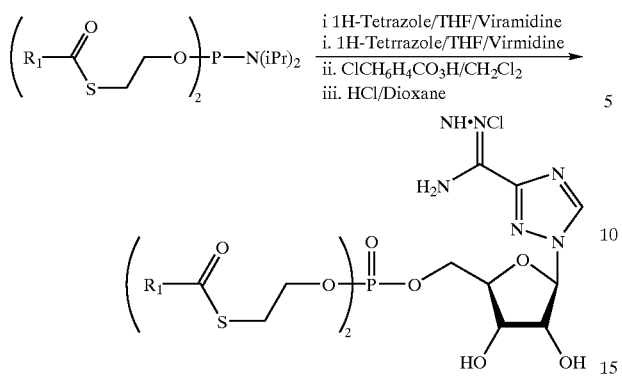

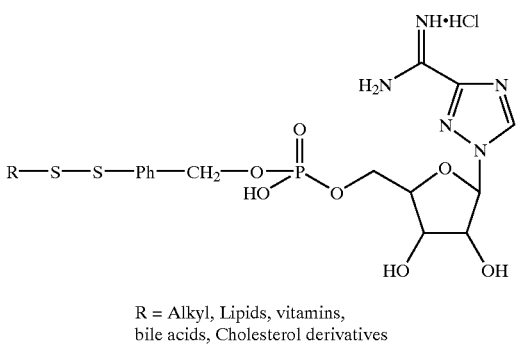

R = Alkyl, Lipids, vitamins, bile acids, Cholesterol derivatives $R_1$ is alkyl groups such as $CH_3C(O)S—CH_2CH_2—$; $(CH_3)_2CHC(O)S—CH_2CH_2—$; $(CH_3)_3CC(O)S—CH_2CH_2—$; $(CH_3)_3CC(O)OCH_2—$; $C_6H_5C(O)S—CH_2CH_2—$ or $HOCH_2CH_2SS—CH_2CH_2—$.

Amino acid phosphoramidates are yet another class of prodrugs that could be synthesized as described below:

Salicylate-based nucleotide prodrugs of Viramidine™ may be obtained by the following Scheme 9.

Scheme 8

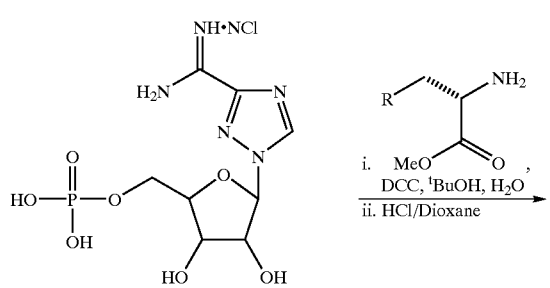

Scheme 9

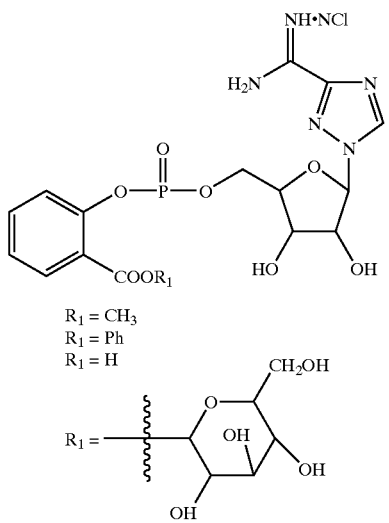

R = Anything Except Hydrogen

Other possible monophosphate prodrugs of Viramidine™ are shown below:

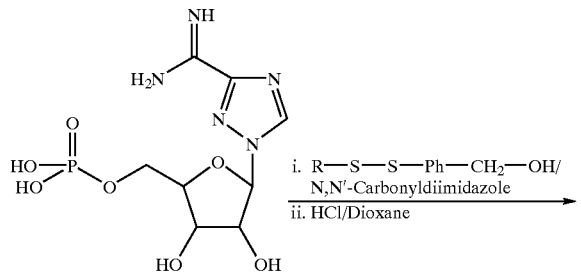

Prodrugs of nucleoside 5'-di or triphosphates would be more interesting since they would bypass more metabolic steps.

Following are potential nucleotide lipophilic prodrugs and may be prepared as depicted below:

Scheme 10
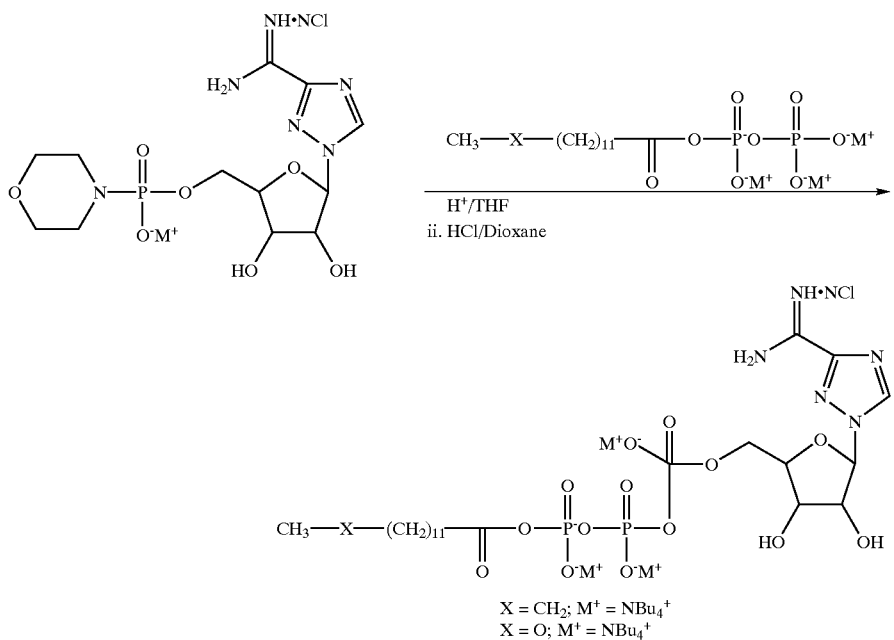
Following are yet another class of potential phosphonate prodrug of viramidine:
Scheme 11
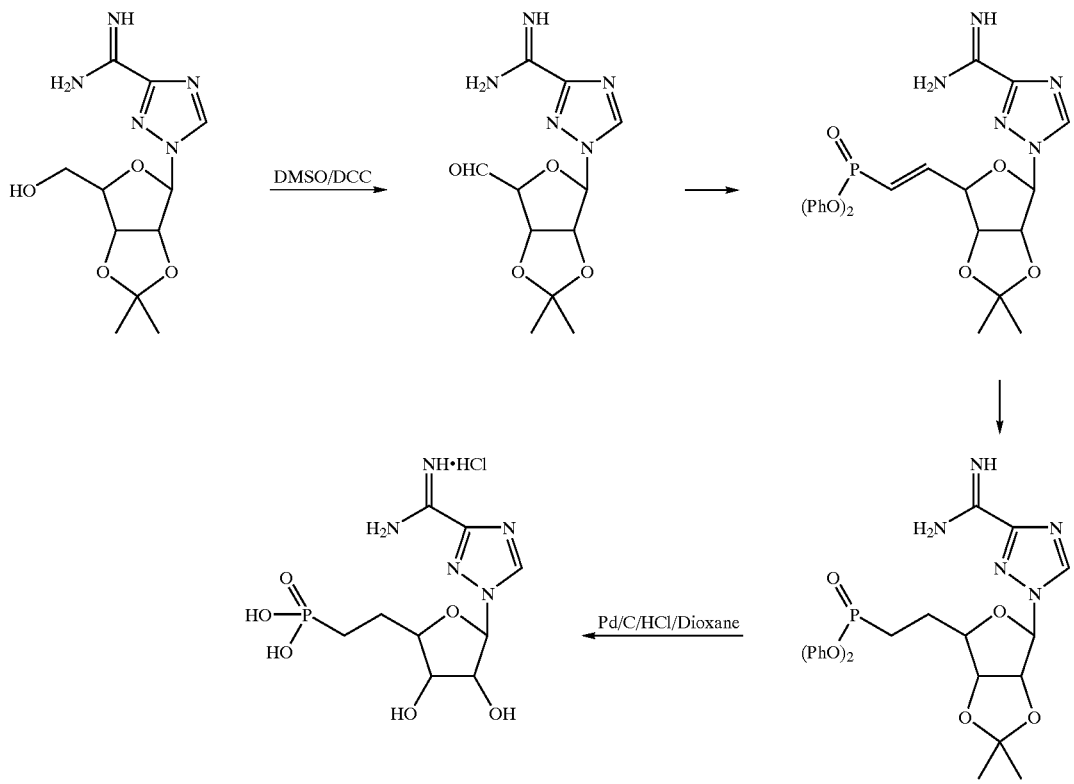

Scheme 12

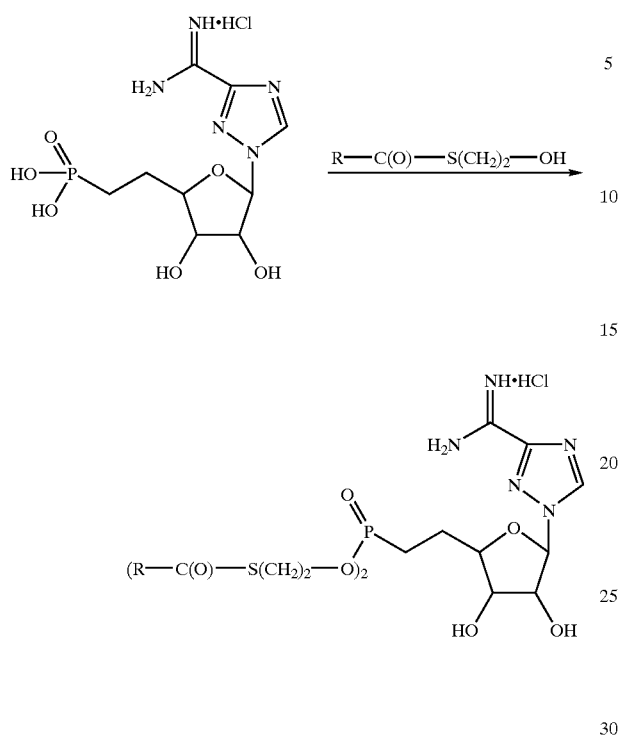

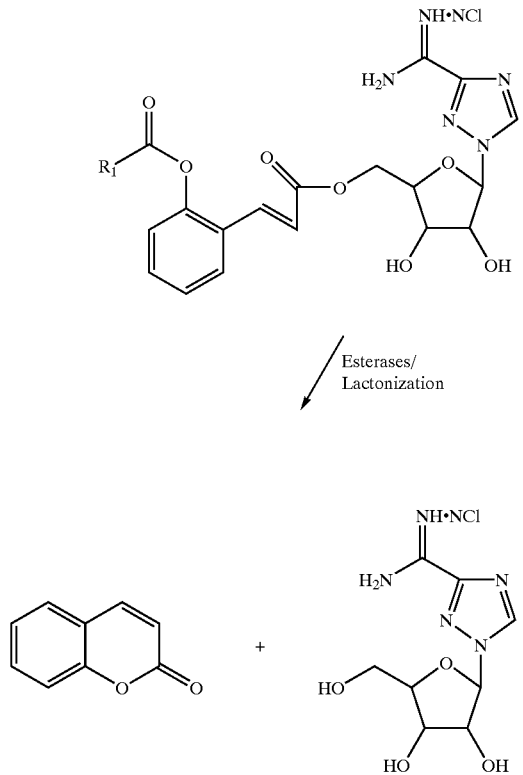

Other possible prodrugs include the possible combinations of the groups shown in PCT patent application WO 98/39342, WO 98/39343, WO 98/39344 and WO 99/45016.

In order for a prodrug to fulfill the requirements necessary to deliver the parent nucleoside into the systemic circulation, the prodrug should be stable to the intestinal environment, it should be permeable to cross the intestinal wall and finally, once II the systemic circulation, has to be labile to be converted back to the parent nucleoside or nucleotide. Because of these properties the choice of ligands that should be attached either to the nucleosides or to the nucleotides to achieve optimized properties is very limited. Based on our idea we propose the following novel nucleoside prodrug approach to Viramidine™ and other nucleoside analogs as well.

Other contemplated pro-drug formations include the following, as shown below: coumarin-based prodrugs, salicylate based prodrugs, dithiosuccinoyl (Dts)-based prodrugs, reductase mediated prodrugs, 4-acyloxybenzyloxycarbonyl-based prodrugs, ras-farnesyl protein transferase prodrugs, succinic acid based prodrugs, and homoserine-based prodrugs:

Scheme 13

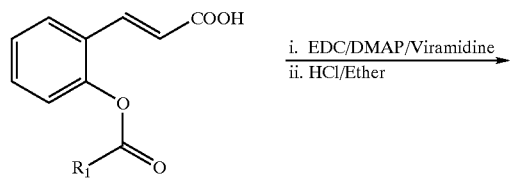

The coumarin based prodrugs are easily cleaved by esterases followed by lactonization releases the parent nucleoside to the target site and been shown in the Scheme 13. $R_1$ is independently $CH_3$, fatty acids, cholesterol, cholic acids, bile acids.

The same coumarinic acid may be used to mask the amidine functionality of Viramidine™ and produce the following prodrug.

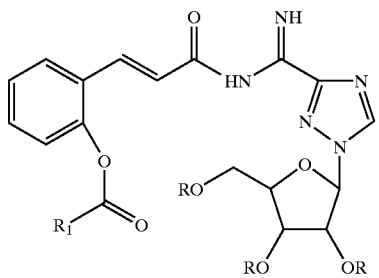

Salicylate based prodrugs should work based on neighboring group catalysis mechanism. Both hydroxyl and amidine masked salicylates are shown below and their synthesis should follow the Scheme 13 by substituting salicylic acid for coumarinic acid. $R_1$ is independently $CH_3$, fatty acids, cholesterol, cholic acids, and bile acids.

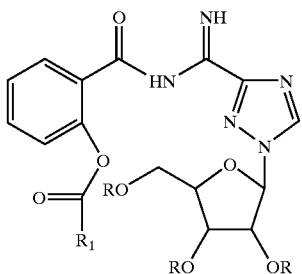

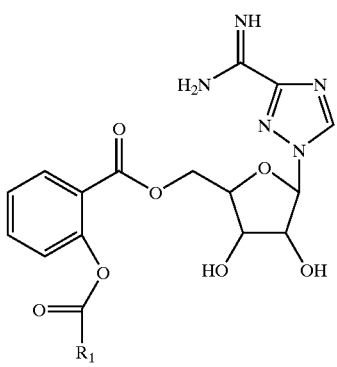

Dithiosuccinoyl (Dts)-based prodrugs are of interest. These prodrugs may give back nucleoside by enzyme-activated cleavage.

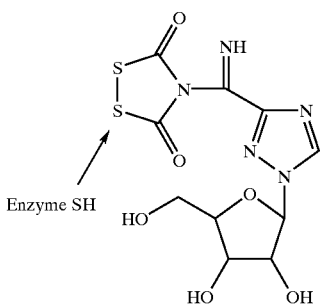

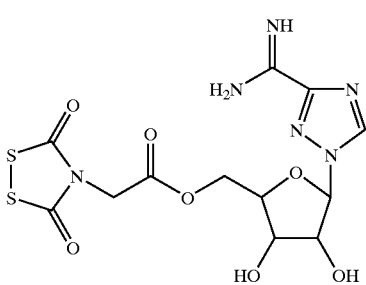

Reductase-mediated prodrugs are cleaved by a combination of esterases and reductases and give back nucleoside. The prodrugs are represented below. $R_1$ is independently $CH_3$, fatty acids, cholesterol, cholic acids, and bile acids.

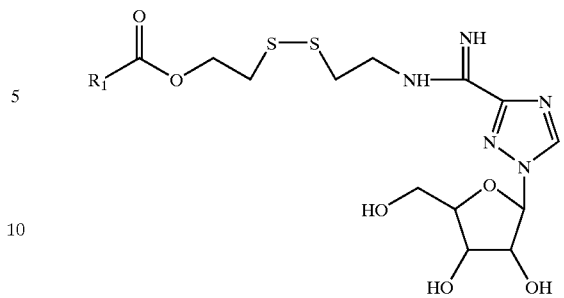

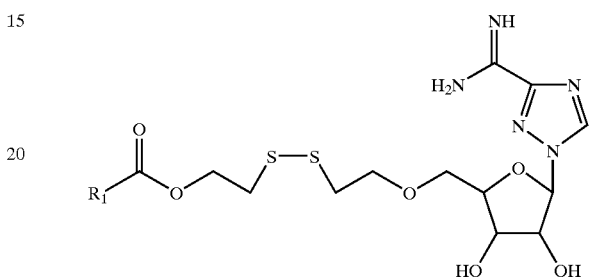

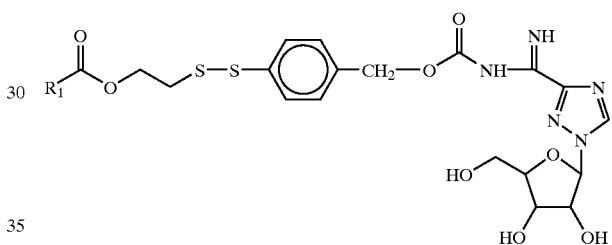

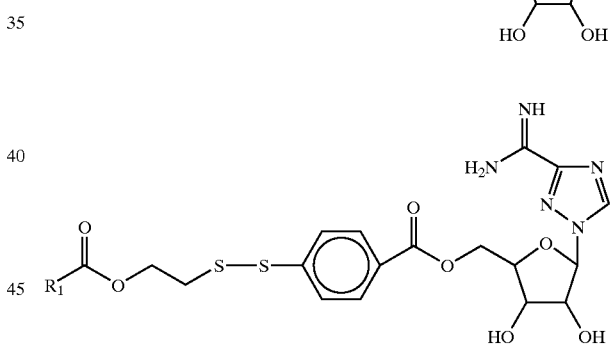

4-Acyloxybenzyloxycarbonyl-based prodrugs may be prepared by using the protecting group strategy used to block amino group of any amino acids and is represented in scheme 14. These prodrugs are cleaved by esterases giving back the free nucleoside. $R_1$ is independently $CH_3$, fatty acids, cholesterol, cholic acids, and bile acids.

Scheme 14

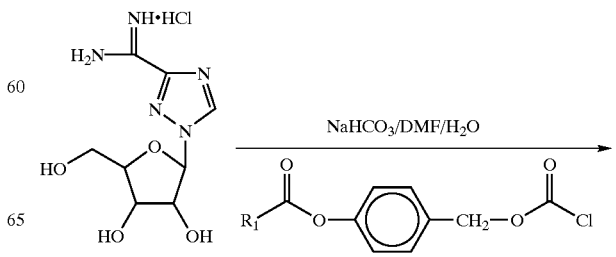

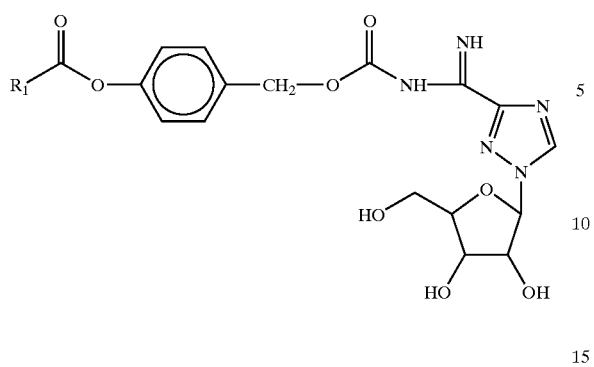

Using Ras-Farnesyl protein transferase prodrugs to target tumor this approach is a viable method. Prodrugs in this type are represented below.

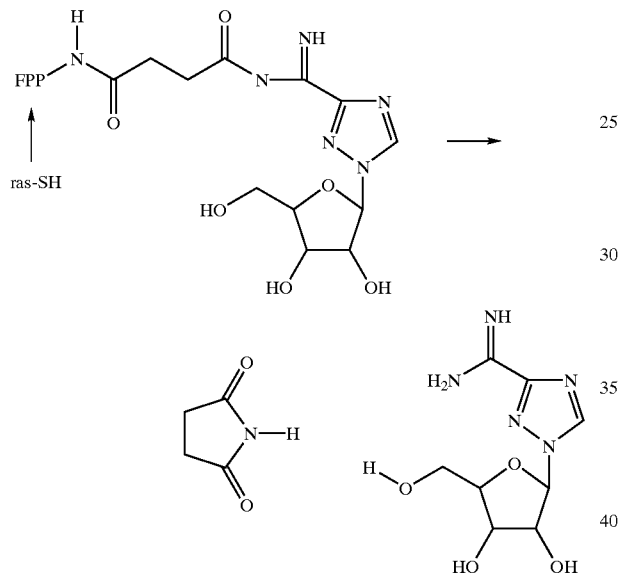

Succinic acid based prodrugs are represented by the following structure. $R_1$ is independently $CH_3$, fatty acids, cholesterol, cholic acids, and bile acids.

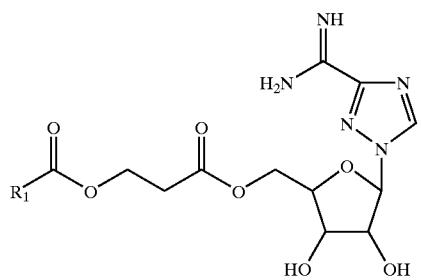

Homoserine-based Prodrugs is yet another novel class of prodiugs and are depicted below. $R_1$ is independently $CH_3$, fatty acids, cholesterol, cholic acids, and bile acids.

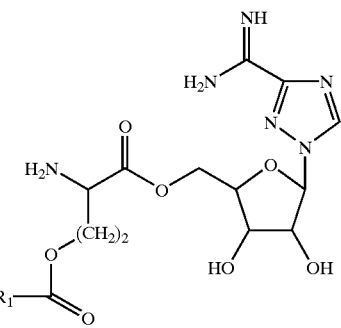

Besides the above said prodrugs, the following type of prodrugs is also part of this invention and a representative example in each group is shown below. $R_1$ is independently $CH_3$, fatty acids, cholesterol, cholic acids, and bile acids.

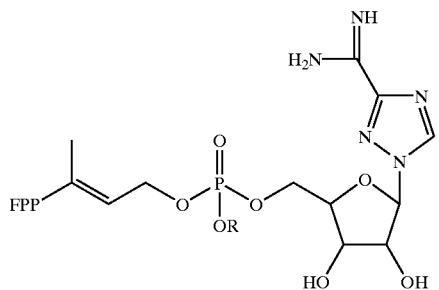

Ras-Farnesyl Protein Transferase

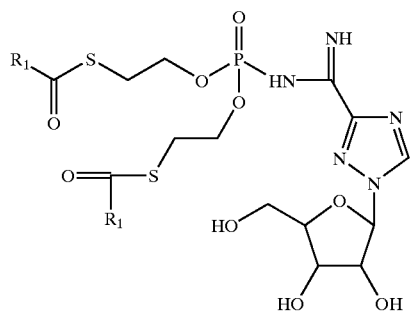

Phosphoramidate-Based

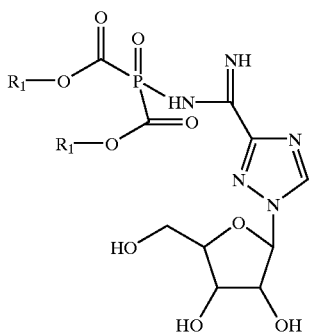

Phosphonoformic acid-Based

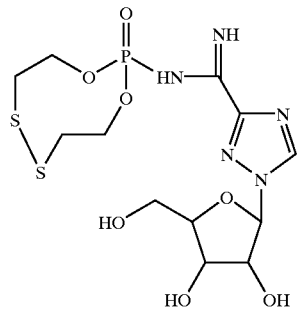

Phosphoramidate-Based

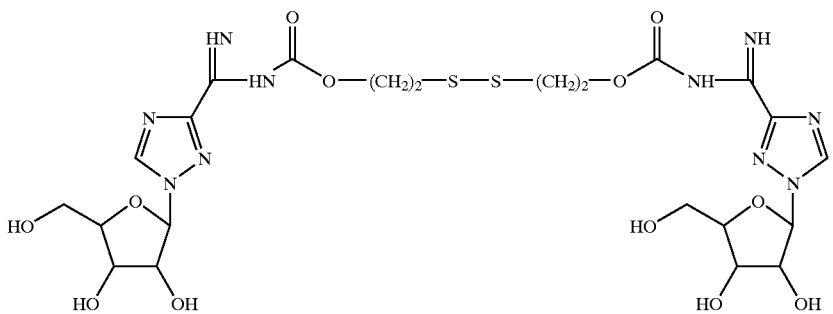

Dimers

Dimers

The new strategies described (1 to 8) above in the nucleoside prodrugs level may easily be adapted to the protected monophosphate prodrugs, phosphonate prodrugs, and triphosphate prodrugs level as well. In addition, the prodrug described so far may be applied equally well to purine, pyrimidine nucleosides and C-nucleosides like tiazofurin, selenazofurin and other related C-nucleosides.

Prodrugs of Viramidine™ could be obtained not only by modifying the sugar portion of the parent molecule but also by derivatizing the amidine functionality too. Following are few classes of prodrugs that may be prepared by modifying the amidine group as described below:

Scheme 15

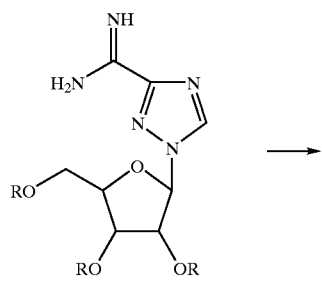

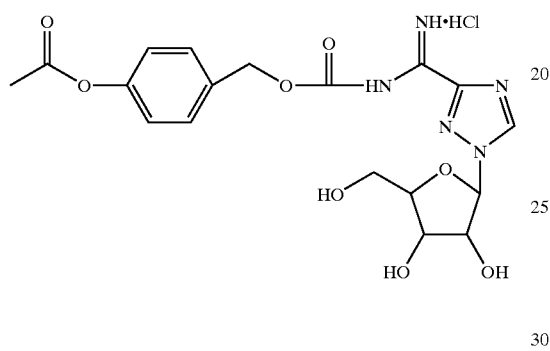

Scheme 16

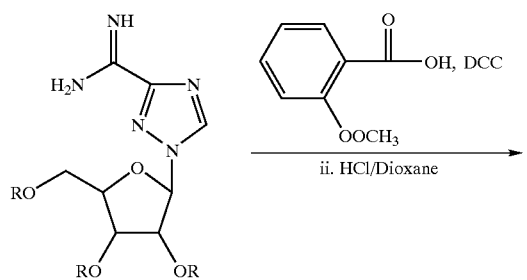

An additional contemplated example of the formation of a pro-drug form of the compounds disclosed herein, such as ribavirin, is as follows.

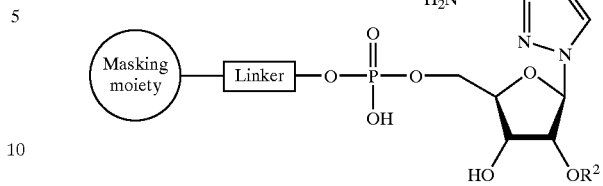

In the above example, the Linker can comprise ligands such as lipids, alkyl groups, bile acid, and vitamins. The Masking Moiety is designed to comprise a masking group that is covalently linked to the Linker.

Examples of the above generalized formula are shown below:

Scheme 1

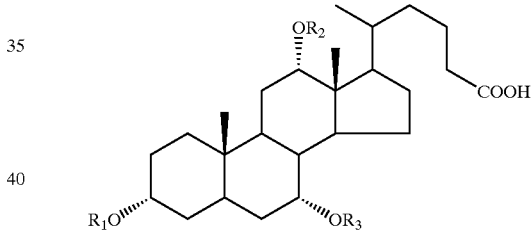

R = Alkyl, Cholesterol, Bile acid, Fat soluble vitamin, or other lipids
L = —C(O)—  or  —OOCCH$_2$CH$_2$CO

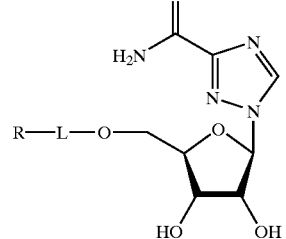

R1 = R2 = R3 = H or Ac
Derivatives of cholic acid

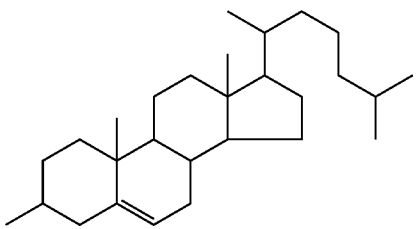

Cholesterol derivative

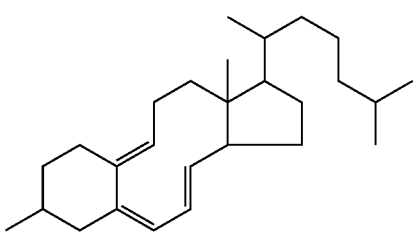

Vitamin D derivative

Scheme 2
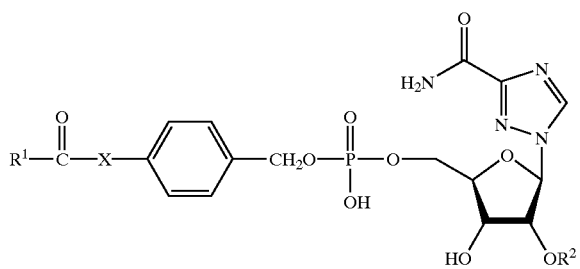
X = O, S
R² = H, Ac
R1 = Alkyl, lipids, bile acids, fat soluble vitamin, etc.
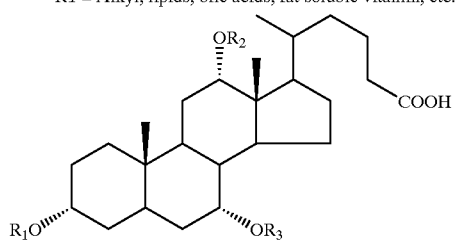
R1 = R2 = R3 = H or Ac
Bile acid or derivatives
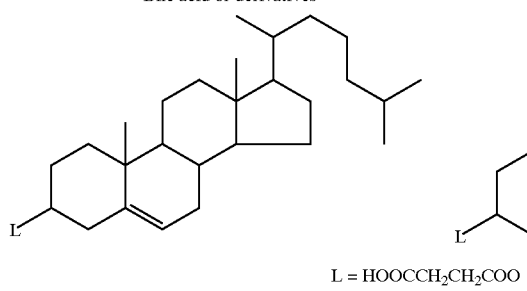
L = HOOCCH₂CH₂COO
Cholesterol derivative
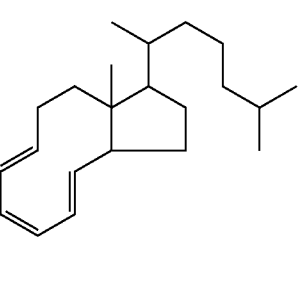
Vitamin D derivative
Scheme 3
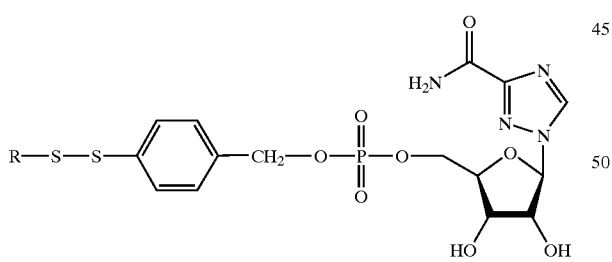
R = Alkyl, Cholesterol, Bile acid, Fat soluble vitamin, or other lipids
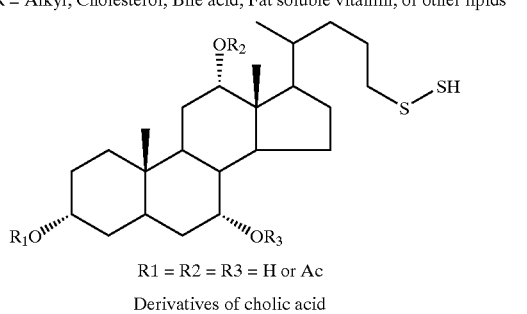
R1 = R2 = R3 = H or Ac
Derivatives of cholic acid
-continued
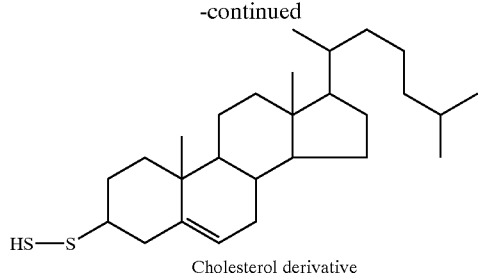
Cholesterol derivative
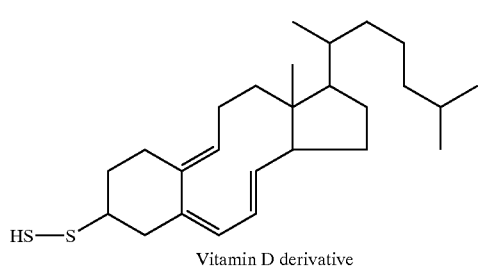
Vitamin D derivative Scheme 4
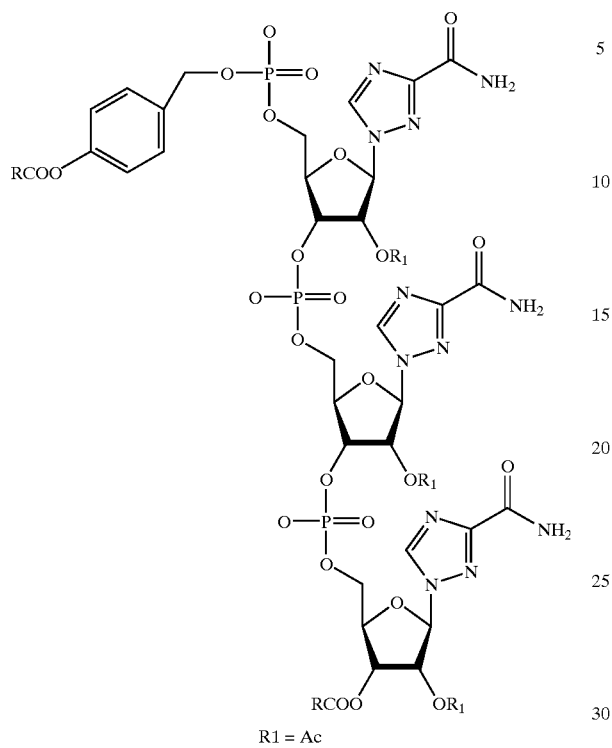
R1 = Ac
Scheme 5
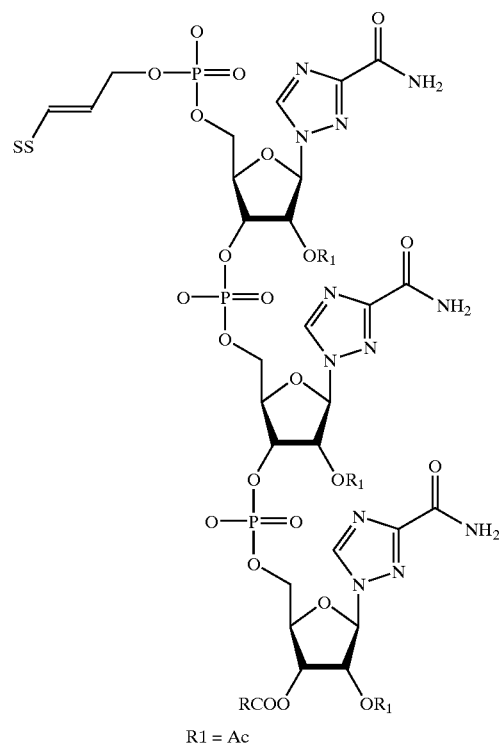
R1 = Ac
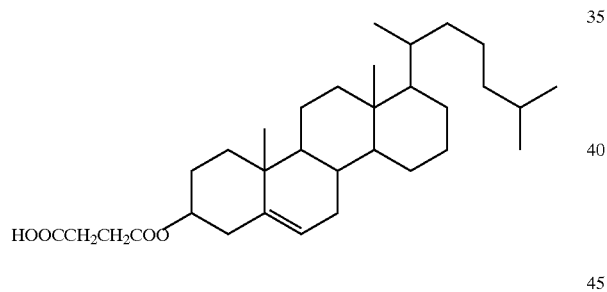
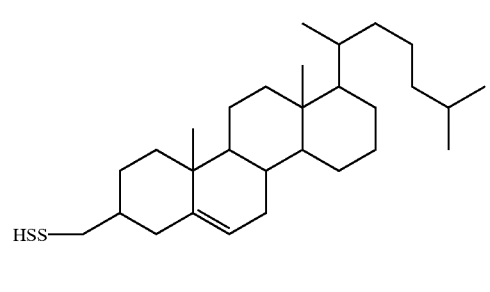
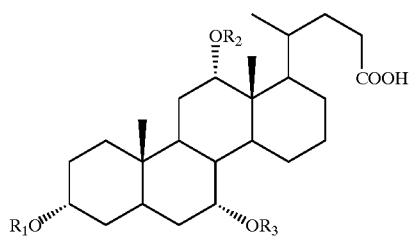
Derivatives of cholic acid
R1 = R2 = R3 = H
R1 = R2 = R3 = Ac
R1 = H, R2 = Ac, R3 = Ac
R1 = Ac R2 = H, R3 = Ac
R1 = R2 = Ac, R3 = H
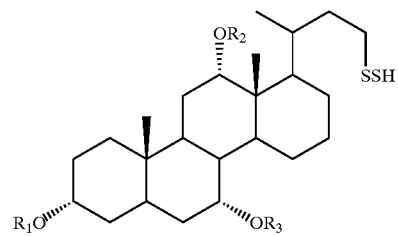
Derivatives of cholic acid
R1 = R2 = R3 = H
R1 = R2 = R3 = Ac
R1 = H, R2 = Ac, R3 = Ac
R1 = Ac R2 = H, R3 = Ac
R1 = R2 = Ac, R3 = H Scheme 6
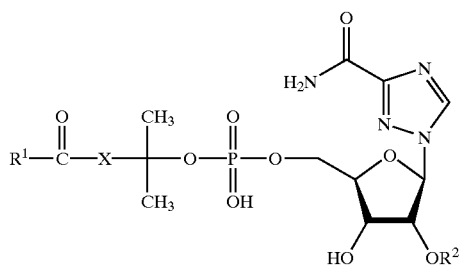
X = O, S
R² = H, Ac
R1 = Alkyl, lipids, bile acids, fat soluble vitamin, etc.
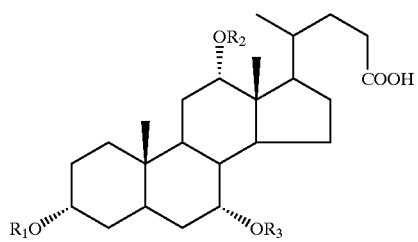
R1 = R2 = R3 = H or Ac
Bile acid or derivatives
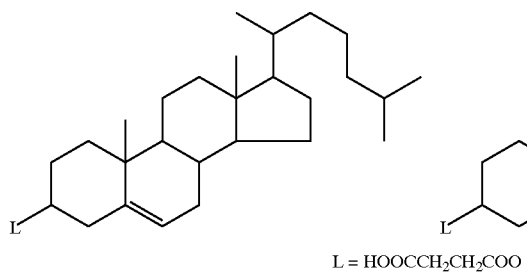
L = HOOCCH₂CH₂COO
Cholesterol derivative        Vitamin D derivative
Scheme 7
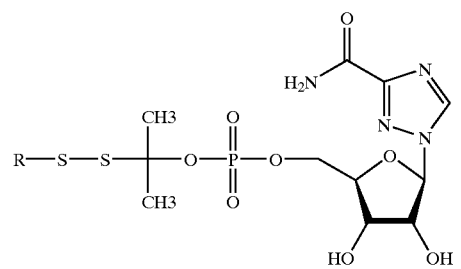
R = Alkyl, Cholesterol, Bile acid, Fat soluble vitamin, or other lipids
-continued
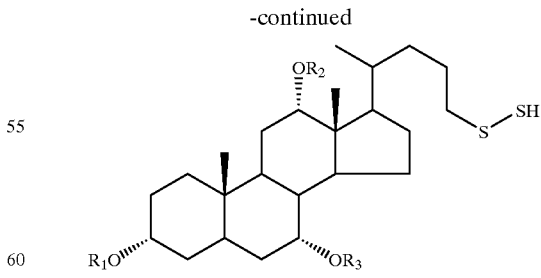
R1 = R2 = R3 = H or Ac
Derivatives of cholic acid

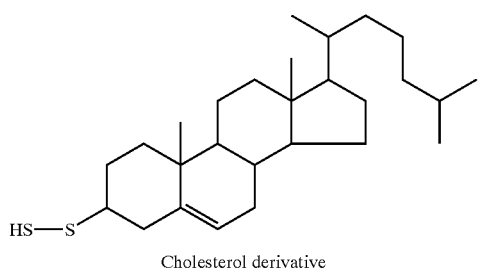

Cholesterol derivative

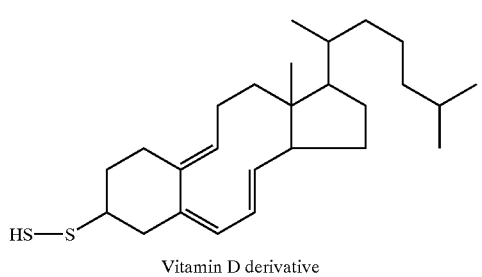

Vitamin D derivative

Contemplated biotransformations for the above synthetic schemes that can be applied to all contemplated nucleoside pro-drugs are as follows:

Scheme 1

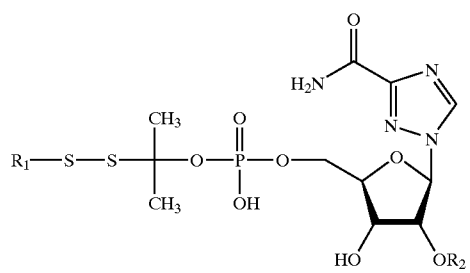

$R_1$ = Lipids, Alkyl, Bile acid,
$R_2$ = H, Ac

↓ Glutathione

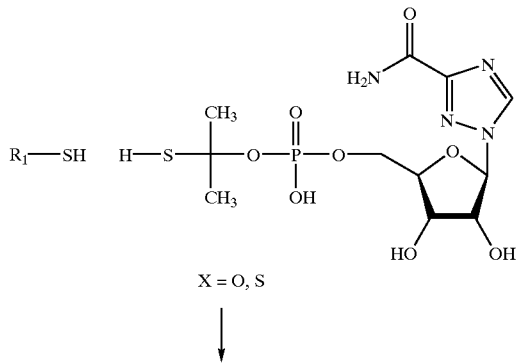

X = O, S

↓

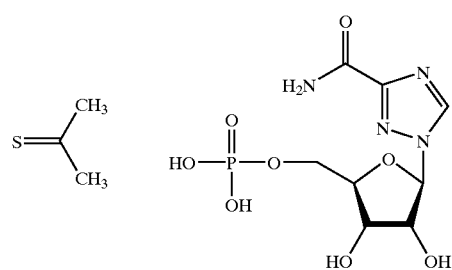

Scheme 2

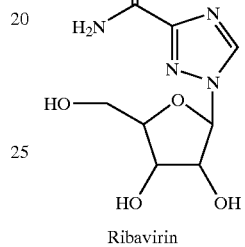

Ribavirin

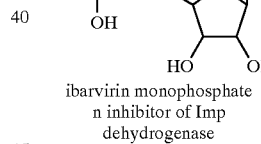

R = H, Acyl, Lipids derivative

↓ Biotransformation 1

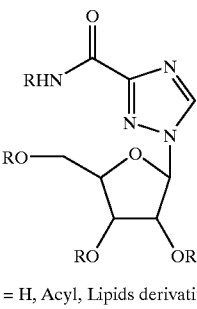

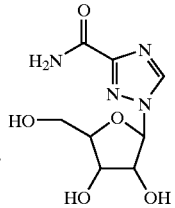

ibarvirin monophosphate n inhibitor of Imp dehydrogenase

Scheme 3

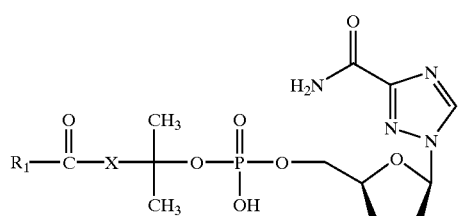

X = O, S
R1 = Lipids, Alkyl, Bile acid,
R2 = H, Ac

↓ lipases, esterases

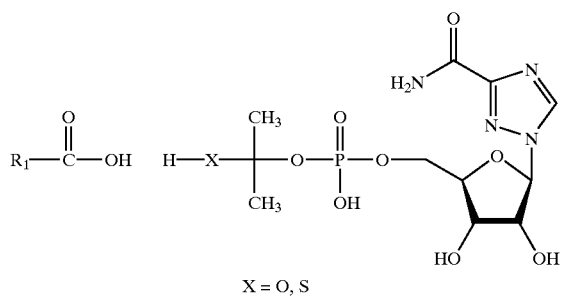

X = O, S

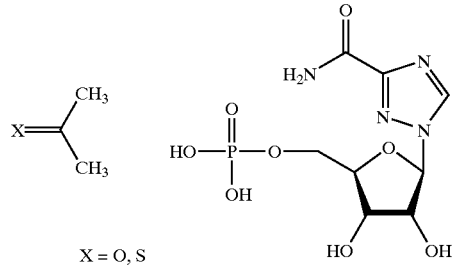

X = O, S

Scheme 4

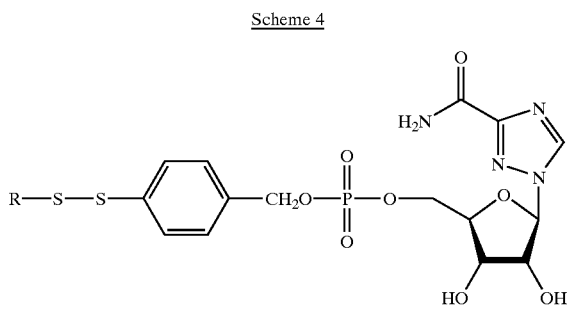

= Alkyl, lipids, vitamin, bile acid, etc.

| Glutathione, nonenzymatica

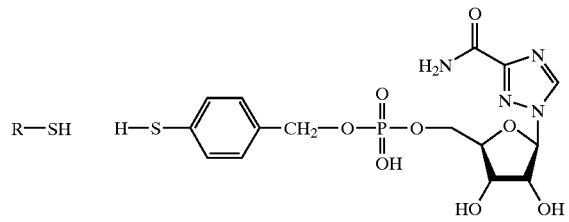

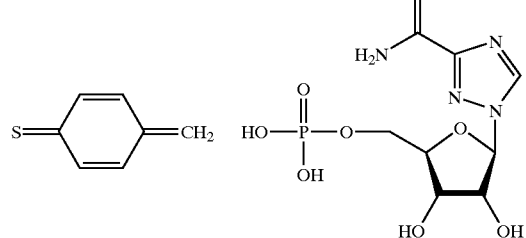

Scheme 5

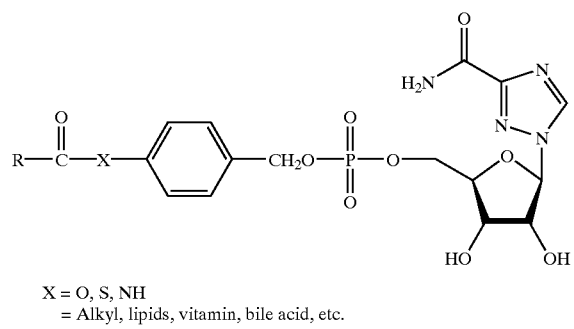

X = O, S, NH
= Alkyl, lipids, vitamin, bile acid, etc.

| lipases, esterases

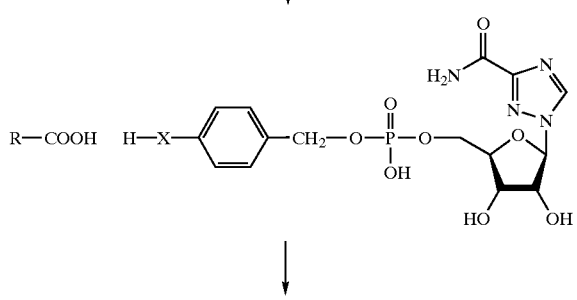

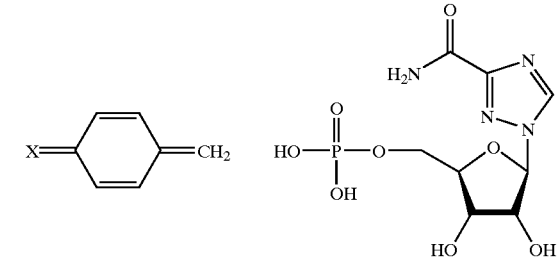

Apart from the above mentioned prodrugs and their contemplated biotransformation schemes, the present invention includes the following combination therapies according to the present invention comprise the administration of at least one compound of the present invention or a functional derivative thereof and at least one other pharmaceutically active ingredient. The active ingredient(s) and pharmaceutically active agents may be administered separately or together and when administered separately this may occur simultaneously or separately in any order. The amounts of the active ingredient(s) and pharmaceutically active agent(s) and the relative timings of administration will be selected in order to achieve the desired combined therapeutic effect. Preferably, the combination therapy involves the administration of one compound of the present invention or a physiologically functional derivative thereof and one of the agents mentioned herein below.

Examples of other drugs or active ingredients contemplated to be effective in combination with a modulator selected from Formula 1 or Formula 2 are anti-viral agents such as interferon, including but not limited to interferon α and γ, ribavirin, acyclovir, and AZT™; anti-fungal agents such as tolnaftate, Fungizone™, Lotrimin™, Mycelex™, Nystatin and Amphoteracin; anti-parasitics such as Mintezol™, Niclocide™, Vermox™, and Flagyl™, bowel agents such as Immodium™, Lomotil™ and Phazyme™; anti-tumor agents such as interferon a and γ, Adriamycin™, Cytoxan™, Imuran™, Methotrexate, Mithracin™, Tiazofurin™, Taxol™; dermatologic agents such as Aclovate™, Cyclocort™, Denorex™, Florone™, Oxsoralen™, coal tar and salicylic acid; migraine preparations such as ergotamine compounds; steroids and immunosuppresants not listed above, including cyclosporins, Diprosone™, hydrocortisone; Floron™, Lidex™, Topicort and Valisone; and metabolic agents such as insulin, and other drugs which may not nicely fit into the above categories, including cytokines such as IL2, IL4, IL6, IL8, IL10 and IL12. Especially preferred primary drugs are AZT, 3TC, 8-substituted guanosine analogs, 2,3-dideoxynucleosides, interleukin II, interferons such as IαB-interferons, tucaresol, levamisole, isoprinosine and cyclolignans.

Examples of such further therapeutic agents include agents that are effective for the modulation of immune system or associated conditions such as AZT, 3TC, 8-substituted guanosine analogs, 2', 3'-dideoxynucleosides, interleukin II, interferons, such as α-interferon, tucaresol, levamisole, isoprinosine and cyclolignans. Certain compounds according to the present invention may be effective for enhancing the biological activity of certain agents according to the present invention by reducing the metabolism or inactivation of other compounds and as such, are co-administered for this intended effect.

With respect to dosage, one of ordinary skill in the art will recognize that a therapeutically effective amount will vary with the infection or condition to be treated, its severity, the treatment regimen to be employed, the pharmacokinetics of the agent used, as well as the patient (animal or human) treated. It is contemplated that various alternative dosages are also appropriate, including dosages between 0.5 mg/kg and 0.1 mg/kg and less, but also dosages between 0.5 and 1.0 mg/kg and more. It is further contemplated that while treatment success may be achieved with some viral infections at relatively low plasma concentrations of the compounds of Formula 1 or Formula 2, other viral infections may require relatively high dosages. It is contemplated, however, that an appropriate regimen will be developed by administering a small amount, and then increasing the amount until the side effects become unduly adverse, or the intended effect is achieved. (FIGS. 1 and 2)

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carrier, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those that aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Thus, specific embodiments and applications of nucleoside analog prodrugs have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

We claim:

1. A nucleoside analog compound of Formula 1, in which the sugar is either in L- or D-configuration:

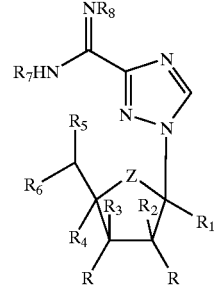

Formula 1 wherein Z is O, $CH_2$, or S;

R is independently H, hydroxyl, protected hydroxyl or halogen;

$R_1$, $R_2$, $R_3$, $R_4$, $R_5$, are independently selected from H, halogen, CN, $CH_2OH$, lower alkyl, vinyl, and acetylene radical; with the proviso that
  when $R_2$ is hydroxyl, then, R that is attached to the same carbon as that of $R_2$ is not halogen;
  when $R_3$ is hydroxyl, then, R that is attached to the same carbon as that of $R_3$ is not halogen;

$R_6$ is selected from H, hydroxyl, protected hydroxyl, —$CH_2OH$, —$CH_2PO(OH)_2$—, O-amino acid radical, O-retinoic acid, O-cholesterol, O-cholic acid, O-coumarinic acid, O-salicylic acid, O-succinic acid, O-bile acid radical, O—P(O)—(O—$CH_2$—$CH_2$—S—CO—$CH_3$)$_2$; O-steroid radical; O-monophosphate derivative radical, O-diphosphate derivative radical, and O-triphosphate derivative radical;

$R_7$ is selected from H, alkyl, $CH_3COO$—, $CH_3COO$-phenyl-$CH_2$—O—CO—, phenyl, —$(CH_2)n$—COOH, coumarinic acid, salicylic acid, dithiosuccinoyl derivative radical, reductase mediated cleavable group, phosphonoformic acid radical, and phosphoramidate group radical;

$R_8$ is selected from H, H*HCl, H*HBr, lower alkyl, phenyl, $CH_3COO-$, $CH_3COO$-Phenyl-$CH_2-O-CO-$, and phenyl;

with the proviso that $R_7$ and $R_8$ are not H at the same time.

2. A nucleoside analog compound of Formula 3, in which the sugar is either in the L- or D-configuration:

Formula 3

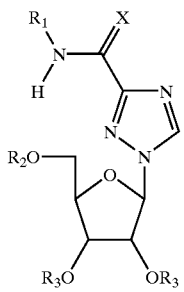

wherein X is O or NH;

$R_1$ is a masking group of the amino group;

$R_2$ is selected from H, HCO—, R—C(O)—, and (R'O)$_2$P(O)—O—, where R is a $C_1$–$C_{17}$ alkyl, alkenyl, or alkynyl group, and R' is a masking group of the phosphate;

$R_3$ is independently H or $C_1$–$C_{18}$ acyl; and $R_1$ and $R_2$ are not hydrogen at the same time.

3. A nucleoside analog compound of Formula 4, in which the sugar is either in the L- or D-configuration:

Formula 4

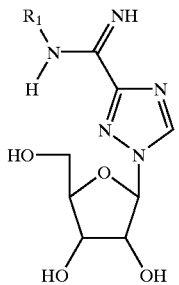

where $R_1$ is a masking group having any of the following structures:

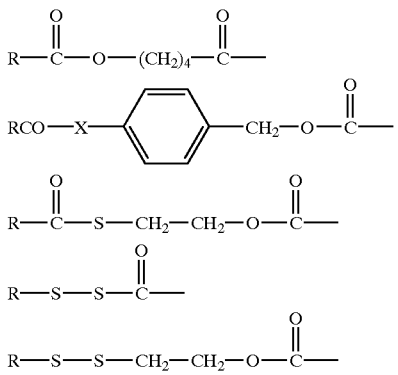

-continued

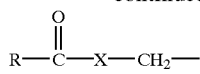

where X is O or S; and

R is straight or branched $C_1$–$C_{18}$ alkyl, alkenyl, alkynyl, aryl, or aralkyl.

4. A nucleoside analog compound of Formula 5, in which the sugar is either in the L- or D-configuration:

Formula 5

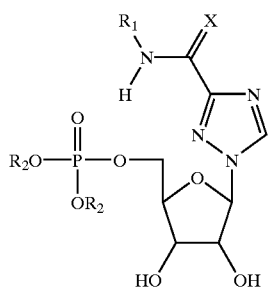

where $R_1$ is H or a masking group as designated in claim 2; $R_2$ is a masking group of the phosphate having any of the following structures:

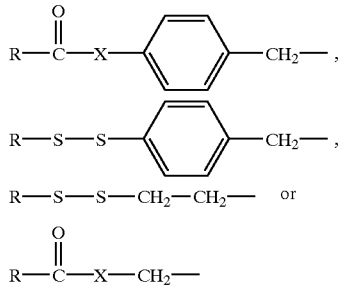

where X is O, or S; and

R is straight or branched $C_1$–$C_{18}$ alkyl, alkenyl, alkynyl, aryl, or aralkyl.

5. A nucleoside analog compound of Formula 7, in which the sugar is either in L- or D-configuration:

Formula 7

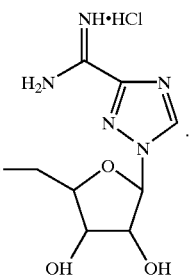

6. A nucleoside analog compound of Formula 10, in which the sugar is either in the L- or D-configuration:

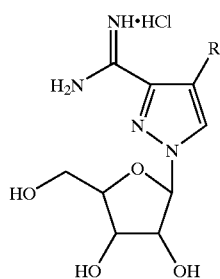
Formula 10
wherein R is selected from hydrogen, halogen, amide, amidine, alkyl, phenyl, vinyl, and acetylene radical.
7. A nucleoside analog compound of Formula 11, in which the sugar is either in the L- or D- configuration:
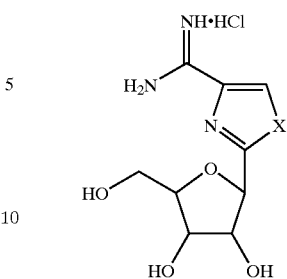
Formula 11
wherein X is selected from oxygen, sulphur, Se, and NR; and R is selected from hydrogen, acetyl, and alkyl.
* * * * *